US012324828B2

(12) United States Patent
Bossard et al.

(10) Patent No.: US 12,324,828 B2
(45) Date of Patent: Jun. 10, 2025

(54) CONJUGATES OF A FACTOR VIII MOIETY HAVING AN OXIME-CONTAINING LINKAGE

(71) Applicant: Nektar Therapeutics, San Francisco, CA (US)

(72) Inventors: Mary J. Bossard, Madison, AL (US); Dawei Sheng, Fremont, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 18/114,710

(22) Filed: Feb. 27, 2023

(65) Prior Publication Data

US 2023/0241181 A1   Aug. 3, 2023

Related U.S. Application Data

(62) Division of application No. 16/319,759, filed as application No. PCT/US2017/043221 on Jul. 21, 2017, now Pat. No. 11,628,205.

(60) Provisional application No. 62/365,836, filed on Jul. 22, 2016.

(51) Int. Cl.
| | |
|---|---|
| *A61K 38/37* | (2006.01) |
| *A61K 47/54* | (2017.01) |
| *A61K 47/60* | (2017.01) |
| *C08G 65/331* | (2006.01) |
| *C08G 65/332* | (2006.01) |
| *C08G 65/333* | (2006.01) |

(52) U.S. Cl.
CPC .............. *A61K 38/37* (2013.01); *A61K 47/54* (2017.08); *A61K 47/60* (2017.08); *C08G 65/3314* (2013.01); *C08G 65/3322* (2013.01); *C08G 65/33306* (2013.01); *C08G 65/33351* (2013.01); *C08G 65/33396* (2013.01)

(58) Field of Classification Search
None
See application file for complete search history.

(56) References Cited

U.S. PATENT DOCUMENTS

| | | | |
|---|---|---|---|
| 4,868,122 | A | 9/1989 | Kominek et al. |
| 5,629,384 | A | 5/1997 | Veronese et al. |
| 5,932,462 | A | 8/1999 | Harris et al. |
| 6,158,888 | A | 12/2000 | Walker et al. |
| 6,362,254 | B2 | 3/2002 | Harris et al. |
| 7,199,223 | B2 | 4/2007 | Bossard et al. |
| 2003/0077752 | A1 | 4/2003 | Cho et al. |
| 2010/0197573 | A1* | 8/2010 | Dorwald ............ A61P 35/00 530/345 |
| 2014/0107320 | A1 | 4/2014 | Haider et al. |
| 2017/0210777 | A1 | 7/2017 | Minami |
| 2021/0369817 | A1 | 12/2021 | Bossard et al. |

FOREIGN PATENT DOCUMENTS

| | | |
|---|---|---|
| EP | 1 688 150 A1 | 8/2006 |
| WO | WO 2008/025856 A2 | 3/2008 |
| WO | WO 2011/017055 A2 | 2/2011 |
| WO | WO 2012/016131 A1 | 2/2012 |
| WO | WO 2015/186988 A1 | 12/2015 |
| WO | WO 2016/036794 A1 | 3/2016 |

OTHER PUBLICATIONS

English Translation of Chinese Rejection Decision corresponding to Chinese Patent Application No. 201780045001.X date of notification Nov. 7, 2022.
English Translation of Korean Grounds for Final Rejection corresponding to Korean Patent Application No. 10-2019-7003562 issuance date Dec. 1, 2022.
English Translation of Korean Grounds for Final Rejection corresponding to Korean Patent Application No. 10-2019-7003562 issuance date May 12, 2023.
Agerso et al., "Pharmacokinetics and pharmacodynamics of turoctocog alfa and N8-GP in haemophilia A dogs", Haemophilia, vol. 18, pp. 941-947, (2012).
Albrecht et al., "Simple Preparation of O-Substituted Hydroxylamines from Alcohols", Synthesis, No. 10, pp. 1635-1638 (2006).
Bader et al., "Polysialic acid: overcoming the hurdles of drug delivery", Ther. Deliv., vol. 5, No. 3, pp. 235-237, (2014).
Baldwin et al., "Synthesis of Polymer-Bound Hemoglobin Samples", Tetrahedron, vol. 37, pp. 1723-1726, (1981).
Berge et al., "Pharmaceutical Salts", Journal of Pharmaceutical Sciences, vol. 66, No. 1, pp. 1-19, (Jan. 1977).
Caliceti et al., "Synthesis and Physicochemical Characterization of Folate-Cyclodextrin Bioconjugate for Active Drug Delivery", Bioconjugate Chem., vol. 14, pp. 899-908, (2003).
Harris et al., "Effect of Pegylation on Pharmaceuticals", Nature Reviews, vol. 2, pp. 214-222, (Mar. 2003).
Kaneda et al., "The use of PVP as a polymeric carrier to improve the plasma half-life of drugs", Biomaterials, vol. 25, pp. 3259-3266, (2004).
Lenting et al., "The disappearing act of factor VIII", Haemophilia, vol. 16, pp. 6-15, (2010).
Lenting et al., "The Life Cycle of Coagulation Factor VIII in View of Its Structure and Function", Blood, vol. 92, No. 11, pp. 3983-3996, (Dec. 1, 1998).
Mertens et al., "Biological activity of recombinant factor VIII variants lacking the central B-domain and the heavy-chain sequence $Lys^{713}$-$Arg^{740}$: discordant in vitro activity", British Journal of Haemotology, vol. 85, pp. 133-142, (1993).

(Continued)

*Primary Examiner* — Thomas S Heard
(74) *Attorney, Agent, or Firm* — Susan T. Evans; Jacqueline F. Mahoney

(57) ABSTRACT

The present disclosure provides conjugates comprising a Factor VIII moiety covalently attached via an oxime-containing linkage to a water-soluble polymer, such as for example, a polyethylene glycol polymer. Methods for preparing and for administering such conjugates, are also provided, as are water-soluble polymer oxyamine reagents useful for preparing the subject conjugates, among other things.

4 Claims, No Drawings

(56) References Cited

OTHER PUBLICATIONS

Ostergaard et al., "Prolonged half-life and preserved enzymatic properties of factor IX selectivity PEGylated on native N-glycans in the activation peptide", Blood, vol. 118, No. 8, pp. 2333-2341, (2011).
Peschke et al., "C-Terminally PEGylated hGH-derivatives", Bioorganic & Medicinal Chemistry, vol. 15, pp. 4382-4395, (2007).
Powell et al., "Safety and pharmacokinetics of a recombinant factor VIII with pegylated liposomes in severe hemophilia A", Journal of Thrombosis and Haemostasis, vol. 6, pp. 277-283, (2008).
Powell, et al., "Safety and prolonged activity of recombinant factor VIII Fc fusion protein in hemophilia A patients", Blood, vol. 119, No. 13, pp. 3031-3037, (2012).
Schulte, "Pioneering designs for recombinant coagulation factors", Thrombosis Research, vol. 128, Suppl 1, pp. S9-S12, (2011).
Sims et al., "A Method for the Estimation of Polyethylene Glycol in Plasma Protein Fractions", Analytical Biochemistry, vol. 107, pp. 60-63, (1980).
Slichter et al., "Preparation of Cryoprecipitated Factor VIII Concentrates", Transfusion, vol. 16, No. 6, pp. 616-626, (Nov.-Dec. 1976).
Stennicke et al., "A novel B-domain O-glycoPEGylated FVIII (N8-GP) demonstrates full efficacy and prolonged effect in hemophilic mice models", Blood, vol. 121, No. 11, pp. 2108-2116, (Mar. 14, 2013).
Stennicke et al., "Generation and biochemical characterization of glycoPEGylated factor VIIa derivatives", Thromb. Haemost., vol. 100, pp. 920-928, (2008).
Szmitkowski et al., "Antihaemophilic Factor (Factor VIII) from Human Granulocytes", Haemotologia, vol. 11, No. 1-2, pp. 177-187, (1977).
Tiede, et al., "Enhancing the pharmacokinetic properties of recombinant factor VIII: first-in human trial of glycoPEGylated recombinant factor VIII in patients with hemophilia A", J. Thromb. Haemost., vol. 11, pp. 670-678, (2013).
Turecek et al., "BAX 855, a PEGylated rFVIII product with prolonged half-life", Hamostaseologie, vol. 32, Suppl 1, pp. S29-S38, (2012).
Turecek et al., "PEGylation of Biopharmaceuticals: A Review of Chemistry and Nonclinical Safety Information of Approved Drugs", Journal of Pharmaceutical Sciences, vol. 105, pp. 460-475, (2016).
Wickerhauser, "Preparation of Antihemophilic Factor from Indated Plasma", Transfusion, vol. 16, No. 4, pp. 345-350, (Jul.-Aug. 1976).
Wolfe et al., "Studies on the Rate and Control of Antibody Oxidation by Periodate", Analytical Biochemistry, vol. 231, pp. 123-130, (1995).
PCT International Search Report corresponding to PCT Application No. PCT/US2017/043221 dated Jan. 25, 2018.
PCT International Preliminary Report on Patentability corresponding to PCT Application No. PCT/US2017/043221 date of mailing Jan. 31, 2019.
English Translation of Notification of the First Office Action corresponding to Chinese Patent Application No. 201780045001.X date of notification Aug. 31, 2021.
English Translation of Notification of the Second Office Action corresponding to Chinese Patent Application No. 201780045001.X date of notification Mar. 30, 2022.
European Communication corresponding to European Patent Application No. 17 748 993.7 date Jan. 28, 2021.
English Translation of Notice of Reasons for Rejection corresponding to Japanese Patent Application No. 2019-502676 mailing date Jul. 26, 2021.
English Translation of Notice of Final Rejection corresponding to Japanese Patent Application No. 2019-502676 mailing date May 31, 2022.
English Translation of Notice of Grounds for Rejection corresponding to Korean Patent Application No. 10-2019-7003562 issuance date Jun. 23, 2022.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005—2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).

\* cited by examiner

CONJUGATES OF A FACTOR VIII MOIETY HAVING AN OXIME-CONTAINING LINKAGE

CROSS-REFERENCE TO RELATED APPLICATIONS

This application is a divisional application of U.S. patent application Ser. No. 16/319,749, filed Jan. 22, 2019, now allowed, which is a 35 U.S.C. § 371 application of International Application No. PCT/US2017/043221, filed on Jul. 21, 2017, designating the United States, and claims the benefit of priority to U.S. Provisional Patent Application No. 62/365,836 filed on Jul. 22, 2016, the contents of which are incorporated herein by reference in their entireties.

FIELD

The present disclosure relates generally to conjugates of a water-soluble polymer and a Factor VIII moiety in which the linkage between the Factor VIII moiety and the water-soluble polymer comprises an oxime (~CH=N—O~). More particularly, a water-soluble polymer such as a polyethylene glycol is covalently attached via an oxime linkage to an oxidized carbohydrate moiety of a Factor VIII molecule. In addition, provided herein are, among other things, methods for synthesizing the conjugates, methods for purifying the conjugates, as well as new polymer-oxyamine reagents, and so forth.

BACKGROUND

Scientists and clinicians face a number of challenges in their attempts to develop active agents into forms suited for delivery to a patient. Active agents that are polypeptides, for example, are often delivered via injection rather than orally. In this way, the polypeptide is introduced into the systemic circulation without exposure to the proteolytic environment of the stomach. Injection of polypeptides, however, has several drawbacks. For example, many polypeptides have a relatively short half-life, thereby necessitating repeated injections, which are often inconvenient and painful. Moreover, some polypeptides can elicit one or more immune responses with the consequence that the patient's immune system attempts to destroy or otherwise neutralize the immunogenic polypeptide. Of course, once the polypeptide has been destroyed or otherwise neutralized, the polypeptide cannot exert its intended pharmacodynamic activity. Thus, delivery of active agents such as polypeptides is often problematic even when these agents are administered by injection.

Some success has been achieved in addressing the problems of delivering active agents via injection. Multiple technologies have been employed to extend the half-life of proteins including genetic fusion of albumin (Schulte, S. (2011), *Thrombosis Research* 128 Suppl 1, S9-12) or the Fc portion of an antibody (Schulte, S. (2011), *Thrombosis Research* 128 Suppl 1, S9-12; Powell, J. S., et al., (2012), *Blood* 119, 3031-3037), non-covalent association with liposomes (Powell, J. S., et al., (2008) *J Thromb Haemost* 6, 277-283) and conjugation to water soluble polymers such as polyethylene glycol (Turecek, P. L., et al., Hamostaseologie 32 Suppl 1, S29-38; Turecek, P. L., et al., (2016), 1 *Pharm. Sci.* 105, 460-475), sialic acid (Bader, R. A., and Wardwell, P. R. (2014) *Therapeutic delivery* 5, 235-237), dextran (Caliceti, P., et al., (2003) *Bioconjugate Chemistry* 14, 899-908), and hydroxyethyl starch (Baldwin, J. E., et al., (1981) *Tetrahedron* 37, 1723-1726), polyvinylpyrrilodone (PVP) (Kaneda, Y., et al., (2004) *Biomaterials* 25, 3259-3266), etc. For example, conjugating an active agent to a water-soluble polymer has resulted in a polymer-active agent conjugate having reduced immunogenicity and antigenicity. In addition, these polymer-active agent conjugates often have greatly increased half-lives compared to their unconjugated counterparts as a result of decreased clearance through the kidney and/or decreased enzymatic degradation in the systemic circulation. As a result of having a greater half-life, the polymer-active agent conjugate requires less frequent dosing, which in turn reduces the overall number of painful injections and inconvenient visits with a health care professional. Moreover, active agents that are only marginally soluble can demonstrate a significant increase in water solubility when conjugated to a water-soluble polymer.

Due to its documented safety as well as its approval by the FDA for both topical and internal use, polyethylene glycol has been conjugated to active agents. When an active agent is conjugated to a polymer of polyethylene glycol or "PEG," the conjugated active agent is conventionally referred to as "PEGylated." The commercial success of PEGylated large molecules such as PEGASYS® PEGylated interferon alpha-2a (Hoffmann-La Roche, Nutley, NJ), PEG-INTRON® PEGylated interferon alpha-2b (Schering Corp., Kennilworth, NJ), and NEULASTA™ PEG-filgrastim (Amgen Inc., Thousand Oaks, CA) demonstrates that administration of a conjugated form of an active agent can have significant advantages over the unconjugated counterpart. PEGylated small molecules, such as MOVANATIK™ (naloxegol) (AstraZeneca Pharmaceuticals LP, Wilmington, DE), have also been commercially successful. Harris et al. have provided a review of some of the effects of PEGylation on pharmaceuticals. Harris et al. (2003) *Nat. Rev. Drug Discov.* 2(3):214-221.

Despite these successes, conjugation of a polymer to an active agent to result in a commercially relevant drug is often challenging. For example, conjugation can result in the polymer being attached at or near a site on the active agent that is necessary for pharmacologic activity (e.g., at or near a binding site). For example, random conjugation at lysines on the amino acid backbone may lead to a significant loss of biological activity. In such cases, a corresponding prolonged circulation time may or may not sufficiently compensate for activity losses. In addition, conjugates that demonstrate increased half-lives may still be improved upon with yet longer half-lives combined, or with a beneficial combination of extended half-life and therapeutic activity.

In the area of bleeding disorders, proteins (such as, for example, Factor VIII) can be administered to a patient to address or otherwise ameliorate the bleeding disorder. Various approaches for PEGylating Factor VIII have been described, with the benefit of (among other things) an increased half-live relative to the unconjugated counterpart. Although successful, conjugation of Factor VIII can be potentially improved by (for example) providing additional conjugates of Factor VIII that improve upon the prior successes. Thus, the present disclosure seeks to solve this and other needs in the art.

SUMMARY

In one or more aspects, provided is a conjugate comprising a Factor VIII moiety covalently attached via an oxime-containing linkage to a water-soluble polymer. More particularly, provided herein is a conjugate comprising one or more water soluble polymers covalently attached to one or more oxidized carbohydrates on a Factor VIII moiety.

For example, in some embodiments, the conjugate has a structure, POLY-X—O—N=CH-FVIII, where POLY is a water-soluble polymer, X is an optional spacer comprising one or more atoms, and FVIII is a Factor VIII moiety, where ~CH-FVIII is a residue of a carbonyl group of an oxidized carbohydrate on the Factor VIII moiety.

Regarding the spacer, in some embodiments, the spacer X is hydrolytically stable. In some further embodiments related to the above, X contains at least one heteroatom selected from O, S, and NH. In yet some additional related embodiments pertaining to each and every one of the foregoing, X has an atom length of from about 5 atoms to about 25 atoms.

In some preferred embodiments of a conjugate as provided herein, the water-soluble polymer is a poly(alkylene oxide).

In yet other embodiments pertaining to the water soluble polymer, the water soluble polymer has a weight-average molecular weight of between 2,000 Daltons to 85,000 Daltons.

In some particular embodiments, a conjugate has a structure:

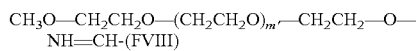
CH$_3$O—CH$_2$CH$_2$O—(CH$_2$CH$_2$O)$_{m'}$—CH$_2$CH$_2$—O—NH=CH-(FVIII)

where (m') ranges from zero to about 4,000 and FVIII is a Factor VIII moiety, where —CH-(FVIII) is a residue of a carbonyl group of an oxidized carbohydrate on the Factor VIII moiety.

In yet one or more further embodiments, the water soluble polymer is branched. In one or more related embodiments, the conjugate has a structure selected from where (m') or (n) for each of the branched structures above independently ranges from about 1 to about 4,000, and X is as previously described in any one or more of the illustrative embodiments. In some embodiments related to the foregoing branched structures, each of (m') or (n) is about 227.

Illustrative Factor VIII moieties for each and every embodiment provided herein include, for example, human recombinant B-domain deleted Factor VIII, as well as human recombinant full length Factor VIII, among others.

Also provided is a composition comprising a Factor VIII moiety covalently attached via an oxime-containing linkage to a water-soluble polymer in accordance with any one or more of the exemplary embodiments described herein and a pharmaceutically acceptable excipient.

In yet another aspect, provided herein is a method comprising administering a composition as described above to a patient, e.g., for treating a blood disorder such as hemophilia A.

In yet another aspect, provided is a polymeric oxyamine reagent having the following structure:

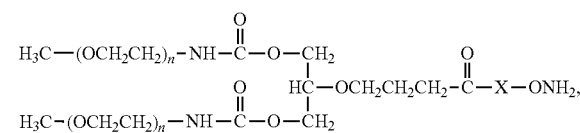

where X is a spacer comprising one or more atoms, and each (n) ranges from about 1 to about 4,000.

In some embodiments related to the oxyamine reagent (or corresponding conjugate), X is or comprises

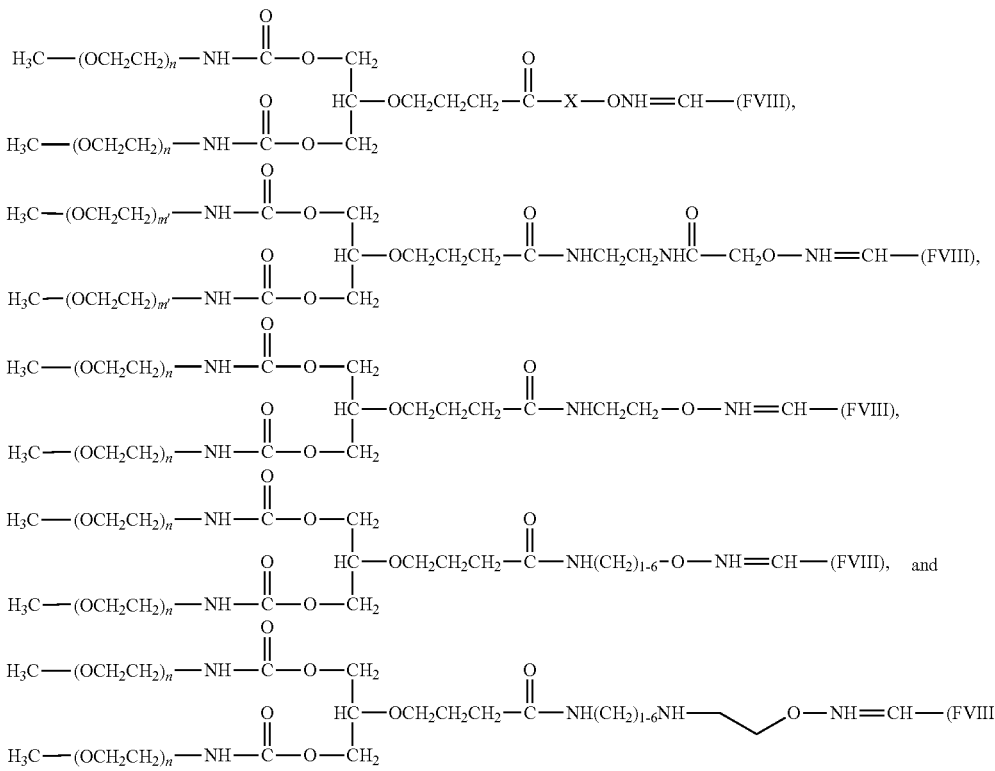

—NH(CH$_2$)$_{1-6}$—. In some particular embodiments, X is or comprises —NH(CH$_2$)$_2$—. In yet some further embodiments, X is —NH(CH$_2$)$_{1-6}$NHC(O)CH$_2$—. In some particular embodiments, X is —NH(CH$_2$)$_2$NHC(O)CH$_2$—.

In one or more further aspects, methods for preparing such conjugates are provided.

In one or more related embodiments, pharmaceutical preparations comprising the conjugates are provided.

In yet another one or more additional aspects, provided herein are methods for preparing a water-soluble polymer having an oxime reactive group, or a reactive water-soluble polymer having a reactive functional group capable of forming an oxime-containing linkage upon reaction with a Factor VIII moiety.

In yet a further aspect, methods for administering the conjugates are provided.

Additional aspects and embodiments are set forth in the following description and claims.

DETAILED DESCRIPTION

In describing and claiming certain features of this disclosure, the following terminology will be used in accordance with the definitions described below unless indicated otherwise.

This disclosure is not limited to particular polymers, synthetic techniques, active agents, and the like, as such may vary.

As used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_m$—," depending upon whether or not the terminal oxygens have been displaced, e.g., during a synthetic transformation. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. Generally, substantially all (and preferably all) monomeric subunits are ethylene oxide subunits, though, the polyethylene glycol polymer may contain distinct end capping moieties or functional groups, e.g., for conjugation. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy) as well as benzyloxy. Additional end-capping moieties include aryl, heteroaryl, cyclo, heterocyclo, and the like. Saturated, unsaturated, substituted and unsubstituted forms of each of the foregoing are envisioned.

An end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

"Non-naturally occurring" with respect to a polymer or water-soluble polymer means a polymer that in its entirety is not found in nature. A non-naturally occurring polymer or water-soluble polymer may, however, contain one or more subunits or portions of a subunit that are naturally occurring, so long as the overall polymer structure is not found in nature.

The term "water-soluble polymer" is any polymer that is soluble in water at room temperature. Typically, a water-soluble polymer will transmit at least about 75%, more preferably at least about 95% of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

Molecular weight in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers described herein are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The terms "spacer" or "spacer moiety" are used herein to refer to an atom or a collection of atoms optionally appearing between one moiety and another.

An "organic radical" as used herein includes, for example, alkyl, substituted alkyl, alkenyl, substituted alkenyl, alkynyl, substituted alkynyl, aryl and substituted aryl.

"Alkyl" refers to a hydrocarbon chain, typically ranging from about 1 to 20 atoms in length. Such hydrocarbon chains may be branched or straight chain, although typically straight chain is preferred. Exemplary alkyl groups include methyl, ethyl, propyl, butyl, pentyl, 1-methylbutyl, 1-ethyl-propyl, 3-methylpentyl, and the like. As used herein, "alkyl" includes lower alkyl.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated cyclic hydrocarbon chain, including bridged, fused, or spiro cyclic compounds, preferably made up of 3 to about 12 carbon atoms, more preferably 3 to about 8 carbon atoms.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like, for one or more hydrogen atoms. "Substituted aryl" is aryl having one or more non-interfering groups as a substituent. For substitutions on a phenyl ring, the substituents may be in any orientation (i.e., ortho, meta, or para). "Substituted ammonium" is ammonium having one or more non-interfering groups (e.g., an organic radical) as a substituent.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), more preferably $C_1$-$C_7$ alkyl.

As used herein, "alkenyl" refers to a branched or unbranched hydrocarbon group of 2 to 15 atoms in length, containing at least one double bond. Exemplary alkenyl include (without limitation) ethenyl, n-propenyl, isopropenyl, n-butenyl, iso-butenyl, octenyl, decenyl, tetradecenyl, and the like.

The term "alkynyl" as used herein refers to a branched or unbranched hydrocarbon group of 2 to 15 atoms in length, containing at least one triple bond. Exemplary alkynyl include (without limitation) ethynyl, n-butynyl, iso-pentynyl, octynyl, decynyl, and so forth.

"Aryl" means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. As used herein, "aryl" includes heteroaryl. An aromatic-containing moiety (e.g., $Ar^1$, $Ar^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in vivo or in vitro. This includes food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient. A preferred biologically active agent is a Factor VIII moiety.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

Certain compounds described herein may exist in particular geometric or stereoisomeric forms. The present disclosure contemplates all such compounds, including where applicable, cis- and trans-isomers, R- and S-enantiomers, diastereomers, (D)-isomers, (L)-isomers, the racemic mixtures thereof, and other mixtures thereof, as falling within the scope of this disclosure.

Additionally, certain compounds, polymers, conjugates, and so forth, may contain a basic functional group, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a compound in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", J. Pharm. Sci. 66:1-19).

The pharmaceutically acceptable salts include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, a compound, polymer, conjugate or the like may contain one or more acidic functional groups and, thus, is capable of forming a pharmaceutically-acceptable salt with a pharmaceutically-acceptable base. The term "pharmaceutically-acceptable salts" in these instances refers to the relatively non-toxic, inorganic and organic base addition salts of such compounds, polymers or conjugates. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethyl amine, diethylamine, ethylenediamine, ethanolamine, diethanolamine, piperazine and the like. (See, for example, Berge et al., supra).

"Multifunctional" in the context of a polymer means a polymer having 3 or more functional groups contained therein, where the functional groups may be the same or different. Multifunctional polymers will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having two or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Substantially" or "essentially" means nearly totally or completely, for instance, 95% or greater of a given quantity.

A basic or acidic reactant described herein includes neutral, charged, and any corresponding salt forms thereof.

The term "patient," or "subject" refers to a living organism suffering from or prone to a condition that can be prevented or treated by administration of a conjugate or composition as provided herein, and includes both humans and animals. Subjects include, but are not limited to, mammals (e.g., murines, simians, equines, bovines, porcines, canines, felines, and the like), and preferably are human.

"Optional" and "optionally" mean that the subsequently described circumstance may or may not occur, so that the description includes instances where the circumstance occurs and instances where it does not.

As used herein, the "halo" designator (e.g., fluoro, chloro, iodo, bromo) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise.

Overview

The random PEGylation of blood factors such as Factor VIII has been previously described, and can lead to therapeutically beneficial products. See, for example, U.S. Pat. No. 7,199,223. However, due to the large number of lysines in a protein such as Factor VIII, random PEGylation can present challenges, for example, in reproducibly preparing conjugate mixtures, characterizing the product, and in forming a product that maintains sufficient bioactivity to be therapeutically useful.

For proteins such as Factor VIII containing carbohydrate groups, PEGylation at the carbohydrates offers the potential for placement of the PEG in locations which may be less likely to interfere with biological activity. Carbohydrate PEGylation using an enzyme to facilitate conjugation of PEG to the carbohydrate portion of a protein has been previously described for the PEGylation of the major blood factors, FVIIa, FIX and FVIII (Ostergaard, H., et al., (2011) *Blood* 118, 2333-2341; Stennicke, H. R., et al., (2008), *Thrombosis and haemostasis* 100, 920-928; Tiede, A., et al., (2013); *J Thromb Haemost* 11, 670-678; Agerso, H., et al., (2012) *Haemophilia* 18, 941-947; Stennicke, H. R., et al., (2013), *Blood* 121, 2108-2116). However, this approach requires the GMP production of additional enzymes for production of the resulting PEGylated protein. While chemical oxidation approaches (i.e., non-enzymatic) for creating a reactive group in the sugar of an O- or N-linked glycan offer a more straightforward approach when compared to enzymatic oxidation, the harsh reaction conditions typically employed are considered to be unsuitable for oxidation of carbohydrate moieties contained in a large blood factor molecule such as Factor VIII, due to the likelihood of significant protein deactivation. While such approaches may have been postulated for Factor VIII, we are unaware of any such oxidation and subsequent conjugation having been successfully carried out, and accompanied by the retention of considerable activity of the Factor VIII moiety. Surprisingly, we have found conditions using classical periodate oxidation of glycols and carbohydrates that enable conjugation of FVIII without the need for additional enzymes or protein engineering, and that does not destroy the activity of the protein. Chemical PEGylation of protein-bound carbohydrates typically requires oxidation of an unreactive sugar hydroxyl into a reactive aldehyde, followed by coupling to an appropriate PEG reagent to achieve a stably linked conjugate.

Mild oxidation (~1 mM) conditions using sodium periodate can selectively oxidize the vicinal hydroxyl groups of N-acetyl-D-neuraminic acid (sialic acid), a terminal sugar found on glycoprotein carbohydrate trees. High concentrations of periodate cleave adjacent hydroxyl-containing carbon bonds on other sugars and can cause undesired ring opening. Careful control of periodate oxidation allows successful selective tritiation of carbohydrate residues for radiolabel biodistribution studies without incorporation of tritium into non-sialic acid parts of the protein.

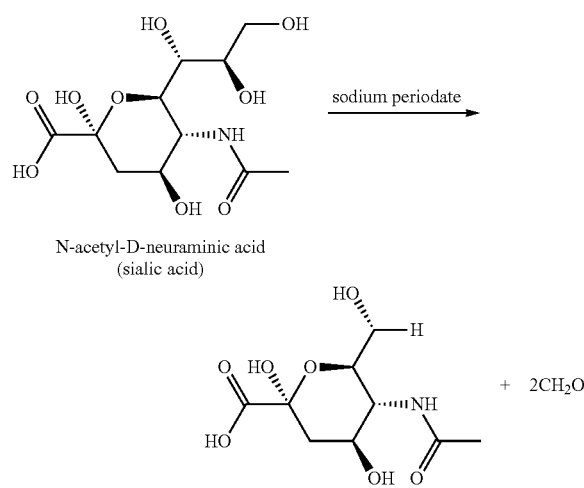

Quenching excess periodate with, for example, a large excess of ethylene glycol followed by rapid removal of the formaldehyde minimizes back reaction with the protein amines (Wolfe, C. A., and Hage, D. S. (1995), *Anal Biochem* 231, 123-130).

As described herein, a preferred coupling for carbohydrate PEGylation entails the use of water-soluble polymer oxyamine reagents that may optionally possess a linker between the PEG and the oxyamine group. In the illustrative reaction scheme below, there is no linker. The oxime linkage is preferred since it is more stable than the linkage obtained with the use of hydrazide-functionalized polyethylene glycol reagents.

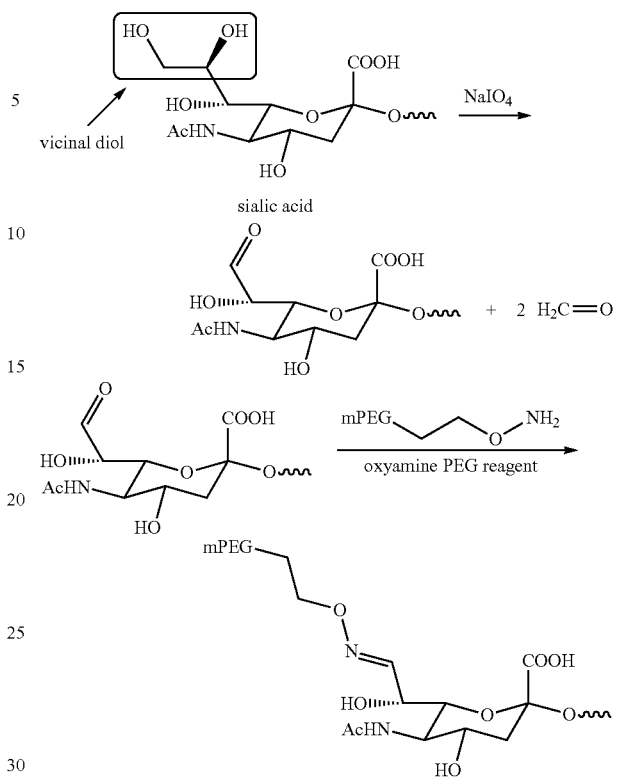

This approach is particularly advantageous for the PEGylation of FVIII based upon attachment to the carbohydrate moieties, based on the fact that there are far fewer carbohydrate moieties (23 chains) than lysines (159) in full length FVIII (Lenting, P. J., van Mourik, J. A., and Mertens, K. (1998) *Blood* 92, 3983-3996). The details surrounding the provision of water-soluble polymer oxime-linked conjugates Factor VIII, the conjugates themselves, related polymeric reagents and related methods are described in the sections which follow.

Water Soluble Polymer

Before describing exemplary conjugates, features of a water-soluble polymer are discussed below. The various embodiments of a water-soluble polymer will each apply to the reactive water soluble polymers, conjugates, compositions, related methods and the like that are the subject of this disclosure.

With respect to a given water-soluble polymer, each water-soluble polymer (e.g., POLY, POLY$^1$ and POLY$^2$) can comprise any polymer so long as the polymer is water-soluble and non-peptidic. Although preferably a poly(ethylene glycol), a water-soluble polymer for use herein can be, for example, other water-soluble polymers such as other poly(alkylene glycols) [also referred to as "poly(alkyleneoxides)"], such as poly(propylene glycol) ("PPG"), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. The water-soluble polymer can be a homopolymer, copolymer, terpolymer, nonrandom block polymer, and random block polymer of any of the foregoing. In addition, a water-soluble polymer can be linear, but can also be in other forms (e.g., branched, forked, and the like) as will be described in further detail below. In the context of being present within an overall structure, a water-soluble polymer has from 1 to about 300 termini.

In instances where the polymeric reagent comprises two or more water-soluble polymers, each water-soluble polymer in the overall structure can be the same or different. It is preferred, however, that all water-soluble polymers in the overall structure are of the same type. For example, it is preferred that all water-soluble polymers within a given structure are poly(ethylene glycol) polymers.

Although the weight-average molecular weight of any individual water-soluble polymer can vary, the weight average molecular weight of any given water-soluble polymer will typically be in the following range: 100 Daltons to about 150,000 Daltons. Exemplary ranges, however, include weight-average molecular weights in the following ranges: in the range of from about 880 Daltons to about 5,000 Daltons; in the range of greater than 5,000 Daltons to about 100,000 Daltons; in the range of from about 6,000 Daltons to about 90,000 Daltons; in the range of from about 10,000 Daltons to about 85,000 Daltons; in the range of greater than 10,000 Daltons to about 85,000 Daltons; in the range of from about 20,000 Daltons to about 85,000 Daltons; in the range of from about 53,000 Daltons to about 85,000 Daltons; in the range of from about 25,000 Daltons to about 120,000 Daltons; in the range of from about 29,000 Daltons to about 120,000 Daltons; in the range of from about 35,000 Daltons to about 120,000 Daltons; in the range of about 880 Daltons to about 60,000 Daltons; in the range of about 440 Daltons to about 40,000 Daltons; in the range of about 440 Daltons to about 30,000 Daltons; and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 440 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 16,000 Daltons, about 17,000 Daltons, about 18,000 Daltons, about 19,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total weight average molecular weight of any of the foregoing can also be used.

When a PEG is the polymeric reagent, the PEG typically comprises a number of (OCH$_2$CH$_2$) monomers [or (CH$_2$CH$_2$O) monomers, depending on how the PEG is defined]. As used throughout the description, the number of repeating units is identified by the subscript "n" in "(OCH$_2$CH$_2$)$_n$." Thus, the value of (n) typically falls within one or more of the following ranges: from 2 to about 3400, from about 4 to about 1500, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

Each water-soluble polymer is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the water-soluble polymers described herein as well as conjugates of active agents and the polymers are biocompatible and non-immunogenic.

In one form, free or nonbound PEG is a linear polymer terminated at each end with hydroxyl groups:

wherein (m') typically ranges from zero to about 4,000, preferably from about 20 to about 1,000. The foregoing PEG is also referred to as PEG diol, and may be used as a starting material for providing PEG reactants suitable for reacting with a Factor VIII moiety, e.g., a carboxyl group of a Factor VIII moiety. In some instances, the number of repeat units in a polyethylene glycol polymer may be designated herein by (n) rather than (m'). In such instances, the illustrative values and ranges of (m') provided herein also apply to (n). The above foregoing polymer, alpha-,omega-dihydroxylpoly(ethylene glycol), can be represented in brief form as HO-PEG-OH where it is understood that the -PEG- symbol can represent the following structural unit:

where (m') is as defined as above.

Another type of free or nonbound PEG useful in, for example, preparing a reactive PEG reagent or a corresponding Factor VIII moiety conjugate having an oxime-containing linker is methoxy-PEG-OH, or mPEG in brief, in which one terminus is the relatively inert methoxy group, while the other terminus is a hydroxyl group. The structure of mPEG is given below.

where (m') is as described above.

Multi-armed or branched PEG molecules, such as those described in U.S. Pat. No. 5,932,462, can also be used as the PEG polymer. For example, PEG can have the structure:

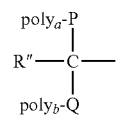

wherein:

poly$_a$ and poly$_b$ are PEGs (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is a methoxy poly(ethylene glycol) disubstituted lysine, and forms, upon reaction with a Factor VIII moiety, a conjugate having an oxime-containing linkage.

In addition, the PEG can comprise a forked PEG. An example of a free or nonbound forked PEG is represented by the following formula:

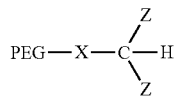

wherein: X is a spacer moiety and each Z is an oxyamine linked to CH by a chain of atoms of defined length. The chain of atoms linking the Z functional groups to the branching carbon atom serve as a tethering group and may comprise, for example, alkyl chains, ether chains, ester chains, amide chains and combinations thereof. U.S. Pat. No. 6,362,254, discloses various forked PEG structures capable of use for providing a Factor VIII moiety conjugate as disclosed herein.

Moreover, the PEG may have a branched form as follows wherein the water-soluble polymer comprises the following branched structure:

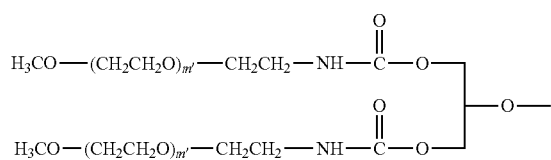

wherein each (m') is independently an integer having a value of from 2 to 4000, or from about 1 to about 3,000, or from 1 to about 2,000, preferably from about 20 to about 1,000.

The PEG polymer may comprise a pendant PEG molecule having reactive groups, such as oxyamine, covalently attached along the length of the PEG rather than at the end of the PEG chain. The pendant reactive groups can be attached to the PEG directly or through a spacer moiety, such as an alkylene group.

It is understood by those of ordinary skill in the art that the term poly(ethylene glycol) or PEG represents or includes all the above forms of PEG.

Those of ordinary skill in the art will recognize that the foregoing discussion concerning substantially water-soluble polymers is by no means exhaustive and is merely illustrative, and that all polymeric materials having the qualities described above are contemplated. As used herein, the term "water-soluble polymer" refers both to a molecule as well as to the water-soluble polymer portion that has been attached to another moiety such as a Factor VIII moiety. The following description of a water-soluble polymer is applicable not only to the polymeric reagent, but to the corresponding conjugates formed using the described polymeric reagents.

The functional group of the water-soluble polymer-containing polymeric reagents used to form the conjugates described herein is an oxyamine, "—O—NH$_2$" (also referred to as an amino-oxy polymer). Thus, the reactive PEG may, in certain instances, optionally contain one or more additional atoms, i.e., a spacer, intervening between the PEG portion of the molecule and the reactive oxyamine as shown below.

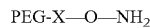

The oxyamine-terminated polymeric reagent can react with carbonyl groups on the Factor VIII moiety (e.g., on the carbohydrates) to provide an oxime linkage between the Factor VIII moiety and the water-soluble polymer such as a polyethylene glycol as previously described. Typically, although not necessarily, the carbonyl group is part of an aldehyde within the Factor VIII moiety (e.g., generated upon oxidation of the Factor VIII moiety). In addition, however, the carbonyl group can be part of a ketone within the Factor VIII moiety. Generically, such reactive PEGs are encompassed by the following formula, PEG-X—O—NH$_2$, as shown above, where PEG may have any of the forms described herein, e.g., linear, branched, forked, and the like, and X is an optional spacer comprised of one or more atoms, and when present, is preferably one that is hydrolytically stable.

Typically, X contains at least one heteroatom such as O, or S, or NH. Illustrative examples are provided below. Generally, X has an atom length of from 1 to about 50 atoms, or from about 4 atoms to about 50 atoms, or from about 5 atoms to about 25 atoms, or even more preferably from about 5 atoms to about 20 atoms, or from 3 to about 15 atoms. Exemplary spacers can include segments such as those independently selected from the group consisting of —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —(CH$_2$)$_3$C(O)NH(CH$_2$)$_2$NHC(O)CH$_2$—CH$_2$—CH$_2$—C(O)—NH—CH$_2$—CH$_2$—NH—C(O)—CH$_2$—, —CH$_2$—CH$_2$—

CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—. For purposes of the present disclosure, however, a series of atoms is not a spacer when the series of atoms is immediately adjacent to a water-soluble polymer segment and the series of atoms is but another monomer, such that the proposed spacer moiety would represent a mere extension of the polymer chain. A spacer or linker as described herein may also comprise a combination of any two or more of the above groups, in any orientation. Illustrative PEG-oxyamines are shown in the table which follows:

TABLE 1

Illustrative PEG Oxyamine Reagents for Forming a Factor VIII-Oxime Glycoconjugate

| Polymeric Reagent | |
|---|---|
| H$_3$CO—(CH$_2$CH$_2$O)$_n$—C(O)—X—ONH$_2$ | (I) |
| H$_2$NO—X—C(O)—CH$_2$CH$_2$—(OCH$_2$CH$_2$)$_n$—O—CH$_2$CH$_2$—C(O)—X—ONH$_2$ | (II) |
| H$_3$C—(OCH$_2$CH$_2$)$_n$—O—CH$_2$CH$_2$—O—NH$_2$ | (III) |
| H$_3$CO—(CH$_2$CH$_2$O)$_n$—CH$_2$CH$_2$NH—C(O)—CH$_2$CH$_2$—C(O)—X—ONH$_2$ | (IV) |
| H$_3$CO—(CH$_2$CH$_2$O)$_n$—CH$_2$CH$_2$SH—CH$_2$CH$_2$—C(O)—X—ONH$_2$ | (V) |
| H$_3$C—(OCH$_2$CH$_2$)$_n$—O—C(O)—X—ONH$_2$ | (VI) |
| H$_3$C—(OCH$_2$CH$_2$)$_n$—NH—C(O)—C$_6$H$_4$—O—C(O)—X—ONH$_2$ | (VII) |
| H$_3$CO—(CH$_2$CH$_2$O)$_n$—C$_6$H$_4$—O—C(O)—X—ONH$_2$ | (VIII) |
| H$_3$C—(OCH$_2$CH$_2$)$_n$—O—C(O)—NH—CH$_2$—CH$_2$—CH$_2$—CH$_2$—CH(NH—C(O)—O—(CH$_2$CH$_2$O)$_n$—CH$_3$)—C(O)—X—ONH$_2$ | (IX) |
| H$_3$C—(OCH$_2$CH$_2$)$_n$—O—CH$_2$C(O)—O—CH(CH$_3$)CH$_2$—C(O)—X—ONH$_2$ | (X) |
| H$_3$CO—(CH$_2$CH$_2$O)$_n$—C(O)—CH$_2$CH$_2$—C(O)—X—ONH$_2$ | (XI) |
| H$_3$CO—(CH$_2$CH$_2$O)$_n$—CH$_2$—CH(CH$_3$)—C(O)—X—ONH$_2$ | (XII) |
| H$_3$CO—(CH$_2$CH$_2$O)$_n$—CH$_2$—CH$_2$—CH(CH$_3$)—C(O)—X—ONH$_2$ | (XIII) |

TABLE 1-continued

Illustrative PEG Oxyamine Reagents for Forming a Factor VIII-Oxime Glycoconjugate Polymeric Reagent (XIV)

$$H_3C-(OCH_2CH_2)_n-NH-\overset{O}{\underset{\|}{C}}-O-CH_2$$
$$H_3C-(OCH_2CH_2)_n-NH-\overset{O}{\underset{\|}{C}}-O-CH_2\underset{|}{\overset{|}{C}H}-OCH_2CH_2CH-\overset{O}{\underset{\|}{C}}-X-ONH_2$$
$$CH_3$$

(XV)

$$H_3C-(OCH_2CH_2)_n-NH-\overset{O}{\underset{\|}{C}}-O-CH_2$$
$$H_3C-(OCH_2CH_2)_n-NH-\overset{O}{\underset{\|}{C}}-O-CH_2\underset{|}{\overset{|}{C}H}-OCH_2CH_2CH-\overset{O}{\underset{\|}{C}}-X-ONH_2$$

(XVI)

$$H_3C-(OCH_2CH_2)_n-O-CH_2CH_2-\overset{O}{\underset{\|}{C}}-X-ONH_2$$

(XVII)

$$H_3C-(OCH_2CH_2)_n-O-CH_2CH_2CH_2-\overset{O}{\underset{\|}{C}}-X-ONH_2$$

(XVIII)

$$H_3C-(OCH_2CH_2)_n-O-\overset{O}{\underset{\|}{C}}NH-(CH_2CH_2O)_4-CH_2CH_2CH_2\overset{O}{\underset{\|}{C}}-X-ONH_2$$

(XIX)

$$\underset{HN}{\overset{O}{\underset{\|}{C}}}-(OCH_2CH_2)_n-O-\overset{O}{\underset{\|}{C}}NH-(CH_2CH_2O)_4-CH_2CH_2CH_2\overset{O}{\underset{\|}{C}}-X-ONH_2$$
$$(CH_2CH_2O)_4-CH_2CH_2CH_2\overset{O}{\underset{\|}{C}}-X-ONH_2$$

(XX)

$$H_3C-(OCH_2CH_2)_n-O-\overset{O}{\underset{\|}{C}}-NH-CH_2-CH_2-CH_2-CH_2$$
$$\overset{H}{\underset{|}{C}}-\overset{O}{\underset{\|}{C}}-NH-(CH_2CH_2O_4)-CH_2CH_2CH_2\overset{O}{\underset{\|}{C}}-X-ONH_2$$
$$H_3C-(OCH_2CH_2)_n-O-\overset{O}{\underset{\|}{C}}-NH$$

(XXI)

$$H_3C-(OCH_2CH_2)_n-NH-\overset{O}{\underset{\|}{C}}-O-CH_2$$
$$\overset{|}{\underset{|}{C}H}-OCH_2CH_2CH_2\overset{O}{\underset{\|}{C}}-NH-(CH_2CH_2O)_4-CH_2CH_2CH_2\overset{O}{\underset{\|}{C}}-X-ONH_2$$
$$H_3C-(OCH_2CH_2)_n-NH-\overset{O}{\underset{\|}{C}}-O-CH_2$$

(XXII)

$$CH_3O(CH_2CH_2O)_n-CH_2$$
$$CH_3O(CH_2CH_2O)_n-\overset{|}{C}H$$
$$H_2C-O\overset{O}{\underset{\|}{C}}-X-ONH_2$$

(XXIII)

$$CH_3O(CH_2CH_2O)_n-CH_2$$
$$CH_3O(CH_2CH_2O)_n-\overset{|}{C}H$$
$$H_2C-O(CH_2CH_2)n-CH_2$$
$$H_2C-O(CH_2CH_2O)n-\overset{|}{C}H$$
$$CH_3O(CH_2CH_2O)_n-\overset{|}{C}H \quad\quad CH_2-O-\overset{O}{\underset{\|}{C}}-X-ONH_2$$
$$CH_3O(CH_2CH_2O)_n-\overset{|}{C}H_2$$

In reference to the PEG reagents provided in Table 1, it is to be understood that the foregoing structures also include pharmaceutically acceptable salt forms thereof, such as the hydrochloride salt. In reference to the structures in Table 1, X is a spacer comprising one or more atoms as described previously herein. In one or more particular embodiments applicable to each of the foregoing structures containing the variable X, spacer X equals or comprises ~NH(CH$_2$)$_{1-6}$~, where the number of methylenes is selected from 1, 2, 3, 4, 5, and 6. More particularly, spacer X equals or comprises ~NH(CH$_2$)$_2$~. Another preferred spacer, applicable to each of the appropriate foregoing structures, is ~NH(CH$_2$)$_2$NHC(O)CH$_2$~. This spacer comprises the segment, ~NH(CH$_2$)$_2$~, along with an additional carboxamide methyl group. More generally, additional particular spacers include, for example, ~NH(CH$_2$)$_{1-6}$NHC(O)CH$_2$~, where the number of intervening methylene groups interposed between the amino groups is selected from 1, 2, 3, 4, 5, and 6. That is to say, in some embodiments, the number of intervening methylenes is 1; in yet some other embodiments, the number is 2; in yet some further embodiments, the number is 3; in yet some other embodiments, the number of 4; in yet some further embodiments, the number is 5; and in some additional embodiments, the number is 6. Moreover, although not shown explicitly, Table 1 above is also meant to explicitly describe, for each of structures I-XXII, the corresponding PEG-Factor VIII moiety (also sometimes referred to herein as FVIII and F8) conjugate wherein for each of structures I-XXII, ~ONH$_2$ is replaced with ~ONH=CH-(FVIII), where the attachment to the Factor VIII moiety is via one or more oxidized carbohydrates of the Factor VIII moiety.

Exemplary polymeric reagents, include for example, those having the following structure:

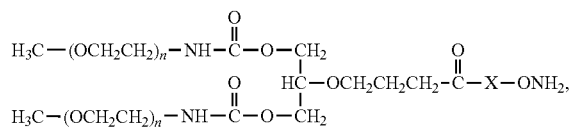

where X is a spacer as generally described above.

Carbonyl groups on the Factor VIII moiety can be present as part of the molecule or can be obtained via modification of a protein having Factor VIII activity. In one approach to modifying a protein having Factor VIII activity, the protein (having at least one glycosylation modification) is subjected to oxidizing conditions (e.g., exposed to periodate or any other suitable oxidizing agent) to thereby oxidize the one or more hydroxy groups contained in the Factor VIII moiety to result in a carbonyl-containing (e.g., aldehyde-containing) Factor VIII moiety—where the carbonyl group is suitable for reaction with a water-soluble polymer oxyamine such as a PEG oxyamine. It has been found that periodate can be used to oxidize vicinal diols in carbohydrates present on the Factor VIII moiety without significantly harming the activity of the protein. Conjugates formed by covalent attachment via an oxime linkage to a carbonyl group (e.g., aldehyde) present on a sugar or carbohydrate portion of a Factor VIII moiety, for example, resulting from oxidation, may sometimes be referred to as glycoconjugates. As mentioned above, due to the significantly fewer carbohydrates in full length Factor VIII (23 chains) when compared to lysines (159), i.e., only 14%, by utilizing the approach described herein, one can arrive at a more highly polymer-directed modified Factor VIII moiety with the water-soluble polymers covalently attached via an oxime-containing linkage, to well-known regions of the Factor VIII molecule. See, for example, FIG. 1 in Lenting, P. J., et al., *Haemophilia* (2010), 16, 6-15, which illustrates the domain structure and post-translational modifications of factor VIII (FVIII). Mature FVIII consists of 2332 amino acids, arranged in a discrete domain structure: A1 (residues 1-336), A2 (373-710), B (741-1648), A3 (1690-2019), C1 (2020-2172) and C2 (2173-2332). The A-domains are bordered by acidic regions a1 (337-372), a2 (711-740) and a3 (1649-1689). The majority of the Cys-residues are engaged in disulphide bridges, while few are present as free cysteines. FVIII is heavily glycosylated with most of the carbohydrate residues residing in the B-domain. The B-domain contains approximately seven O-linked glycans (the exact position of which is unknown) and 16 sites for N-linked glycosylation. Five N-linked glycans are found in the other domains, two of which are mannose-type glycans. Thus, the Factor VIII polymer-modification approach described herein, in particular when using full length Factor VIII, is effective to focus the majority of the PEG attachments in the B-domain by virtue of this domain being heavily glycosylated.

Additional exemplary polymeric reagents will now be discussed in further detail. It must be remembered that while stereochemistry is not specifically shown in any formulae or structures (whether for a polymeric reagent, conjugate, or any other formula or structure), the provided formulae and structures contemplate both enantiomers, as well as compositions comprising mixtures of each enantiomer in equal amounts (i.e., a racemic mixture) and unequal amounts.

An exemplary linear polymeric reagent has the following structure:

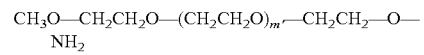

where (m') typically ranges from zero to about 4,000, or from about zero to about 3,000, or from about 0 to about 2,000, preferably from about 20 to about 1,000. Particular illustrative linear PEG oxyamines having a structure as shown above will have molecular weights of, for example, about 5,000 daltons, about 10,000 daltons, about 20,000 daltons, or about 30,000 daltons. The foregoing linear PEG oxyamine is absent a spacer; in this PEG reagent, the polyethylene glycol is covalently attached to the oxyamine group. Polymeric reagents encompassed within this formula can be synthesized following the approaches described in the literature and can be obtained commercially (from, for example, JenKem Technology USA, Plano, TX). For example, PEG oxyamine can be prepared from methoxy-PEG (i.e., by conversion of the terminal hydroxyl group) by O-alkylation of the tert-butyl N-hydroxycarbamate with the PEG-O-methanesulfonate, followed by acidic N-deprotection as described in S. Albrecht, et al, *Synthesis,* 2006, 1635-1638. Representative Factor VIII moiety conjugates prepared using such polymeric reagents are described in the supporting examples.

Additional illustrative branched PEG oxyamine reagents include the following:

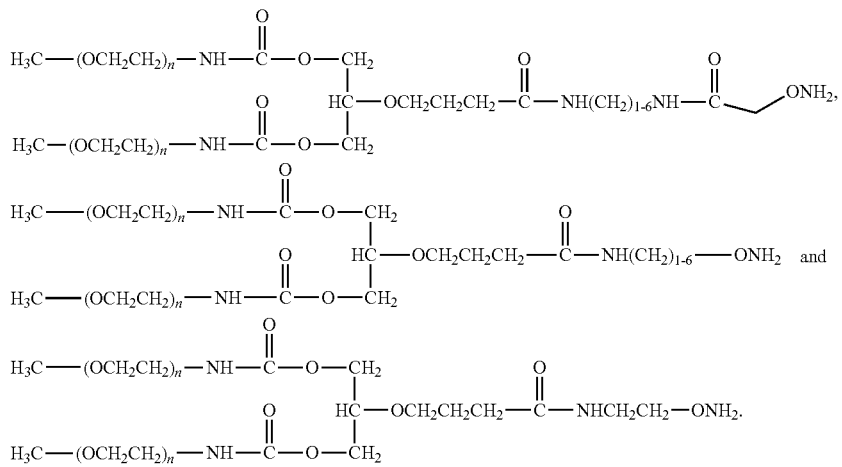

Another exemplary PEG oxyamine reagent has the following branched structure:

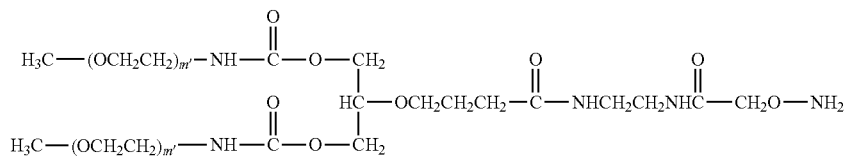

where (m') or (n) for each of the structures provided herein typically ranges from about 1 to about 4,000, or from about 1 to about 3,000, or from 1 to about 2,000, preferably from about 20 to about 1,000. This branched PEG reagent is at times referred to herein as RU-PEG2-oxyamine. Particular branched PEGs having the structure above will possess two PEG "arms" each having a molecular weight of about 10,000 daltons, such that (m') is about 227 in each of the PEG arms. Additional illustrative branched PEG oxyamines according to the foregoing structure possess two PEG "arms" or branches, each having a molecular weight of about 5,000 daltons, or 10,000 daltons (as previously described), or 20,000 daltons, or the like. In the branched structure above, the two PEG arms, $CH_3$—$(OCH_2CH_2O)_m$~, extend from an organic core that is 2-(4-((2-(2-(aminooxy)acetamido)ethyl)amino)-4-oxobutoxy)propane-1,3-diyl dicarbamate. In the branched structure shown above, the segment or spacer intervening between the branched PEG and the oxyamine group is ~$(CH_2)_3C(O)NH(CH_2)_2NHC(O)CH_2$~, although any suitable spacer may be used as described above.

With respect to a Factor VIII moiety (e.g., for reaction with a water-soluble polymer oxyamine such a PEG oxyamine), the Factor VIII moiety useful for the present invention includes any protein that has the same activity (although not necessarily the same degree of activity) as native, human Factor VIII and is glycosylated (i.e., includes sugar residues, such as monosaccharides, linked glycosidically). Included as a possible Factor VIII moiety is native, human Factor VIII, which is a 2,351 amino acid, single chain glycoprotein that is structurally organized as A1-A2-B-A3-C1-C2. When the expressed polypeptide is translocated into the lumen of the endoplasmic reticulum, however, a 19-amino acid signal sequence is cleaved, resulting in a second sequence. This second sequence, herein provided lacks the leading 19 amino acids. It will be appreciated that a Factor VIII moiety for use herein It will be appreciated that a Factor VIII moiety is not limited to merely "active" forms of Factor VIII (e.g., Factor VIIIa) and that the term "Factor VIII moiety" encompasses "precursor" forms as well as other substances that having a similar procoagulant effect.

For any given moiety, it is possible to determine whether that moiety has Factor VIII activity. For example, several animal lines have been intentionally bred with the genetic mutation for hemophilia such that an animal produced from such a line has very low and insufficient levels of Factor VIII. Such lines are available from a variety of sources such as, without limitation, the Division of Laboratories and Research, New York Department of Public Health, Albany, NY and the Department of Pathology, University of North Carolina, Chapel Hill, NC. Both of these sources, for example, provide canines suffering from canine hemophilia A. In order to test the Factor VIII activity of any given moiety in question, the moiety is injected into the diseased animal, a small cut made and bleeding time compared to a untreated diseased animal as a control. Another method useful for determining Factor VIII activity is to determine cofactor and procoagulant activity. See, for example, Mertens et al. (1993) Brit. J. Haematol. 85:133-42. Other methods known to those of ordinary skill in the art can also be used to determine whether a given moiety has Factor VIII activity. Such methods are useful for determining the Factor VIII activity of both the moiety itself (and therefore can be used as a "Factor VIII moiety") as well as the corresponding polymer-moiety conjugate having an oxime-containing linkage.

Nonlimiting examples of Factor VIII moieties include the following: Factor VIII; Factor VIIIa; Factor VIII:C; Factor VIII:vWF; B-domain deleted Factor VIII (and other truncated versions of Factor VIII); hybrid proteins, such as those described in U.S. Pat. No. 6,158,888; glycosylated proteins having Factor VIII activity, such as those described in U.S. Patent Application Publication No. US2003/0077752; and peptide mimetics having Factor VIII activity. Preferred truncated Factor VIII versions (encompassed by the term "B-domain deleted Factor VIII) corresponds to a protein having the amino acid sequence of human Factor VIII having a deletion corresponding to at least 581 amino acids within the region between $Arg^{759}$ and $Ser^{1709}$, more preferably wherein the deletion corresponds to one of the region between $Pro^{1000}$ and $Asp^{1582}$, the region between $Thr^{778}$ and $Pro^{1659}$, and the region between $Thr^{778}$ and $Glu^{1694}$.

With respect to Factor VIII moieties, biologically active fragments, deletion variants, substitution variants or addition variants of any of the foregoing that maintain at least some degree of Factor VIII activity can also be used.

The Factor VIII moiety can advantageously be modified to include one or more amino acid residues such as, for example, lysine, cysteine and/or arginine, in order to provide facile attachment of the polymer to an atom within the side chain of the amino acid, so long as the attachment is an oxime-containing attachment. Techniques for adding amino acid residues are well known to those of ordinary skill in the art.

Moreover, the active agent can be obtained from blood-derived sources. For example, Factor VIII can be fractionated from human plasma using precipitation and centrifugation techniques known to those of ordinary skill in the art. See, for example, Wickerhauser (1976) *Transfusion* 16(4): 345-350 and Slichter et al. (1976) *Transfusion* 16(6):616-626. Factor VIII can also be isolated from human granulocytes. See Szmitkoski et al. (1977) *Haematologia (Budap.)* 11(1-2):177-187.

In addition, the active agent can also be obtained from recombinant methods. Briefly, recombinant methods involve constructing the nucleic acid encoding the desired polypeptide or fragment, cloning the nucleic acid into an expression vector, transforming a host cell (e.g., bacteria, yeast, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art. See, for example, U.S. Pat. No. 4,868,122.

The above exemplary Factor VIII moieties are meant to encompass, where applicable, analogues, agonists, antagonists, inhibitors, isomers, and pharmaceutically acceptable salt forms thereof. In reference to peptides and proteins, this disclosure is intended to encompass synthetic, recombinant, native, glycosylated, and non-glycosylated forms, as well as biologically active fragments thereof. In addition, the term "active agent", in reference to a Factor VIII moiety, is intended to encompass the active agent prior to conjugation as well as the active agent "residue" following conjugation.

The following provides a general schematic of a typical conjugation reaction as provided herein for a Factor VIII moiety:

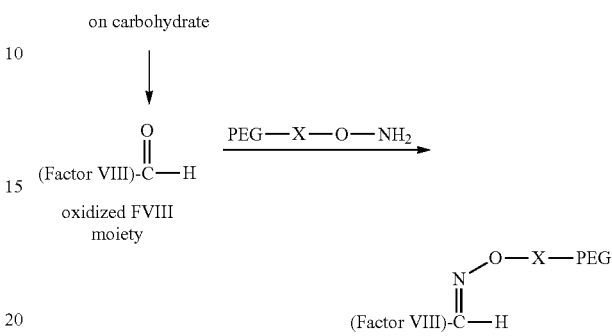

Exemplary conjugates include those of the following formulae

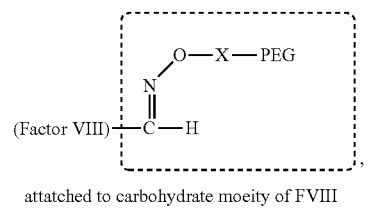

attatched to carbohydrate moeity of FVIII where PEG encompasses any PEG moiety, and in particular, those described herein, and X is an optional spacer moiety as described in detail above. Suitable and exemplary molecular weight values for the PEG moieties attached to the Factor VIII moiety via an oxime-containing linkage are described above. For example, one illustrative Factor VIII moiety conjugate is described generally as follows, where spacer X is absent from the general formula:

$CH_3O-CH_2CH_2O-(CH_2CH_2O)_{m'}-CH_2CH_2-O-NH=CH-(FVIII)$ where (m') typically ranges from zero to about 4,000 and F8 is a residue of a carbonyl-containing Factor VIII moiety. That is to say, the "CH" of the oxime represents the carbon atom of the carbonyl group of the Factor VIII moiety prior to reaction with the PEG-oxyamine reagent.

Further illustrative Factor VIII moiety conjugates include, for example,

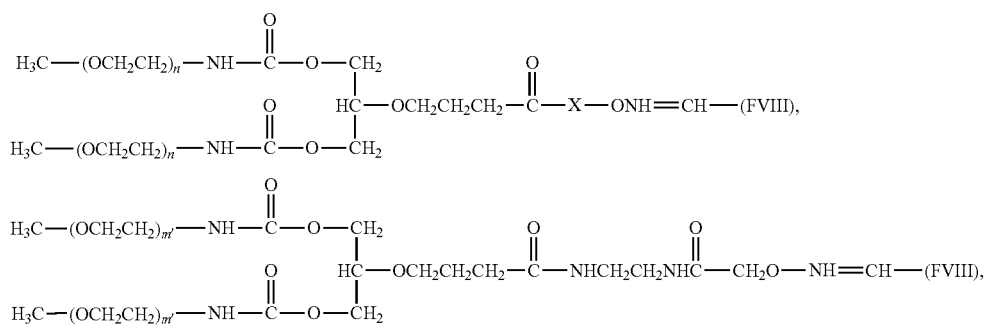

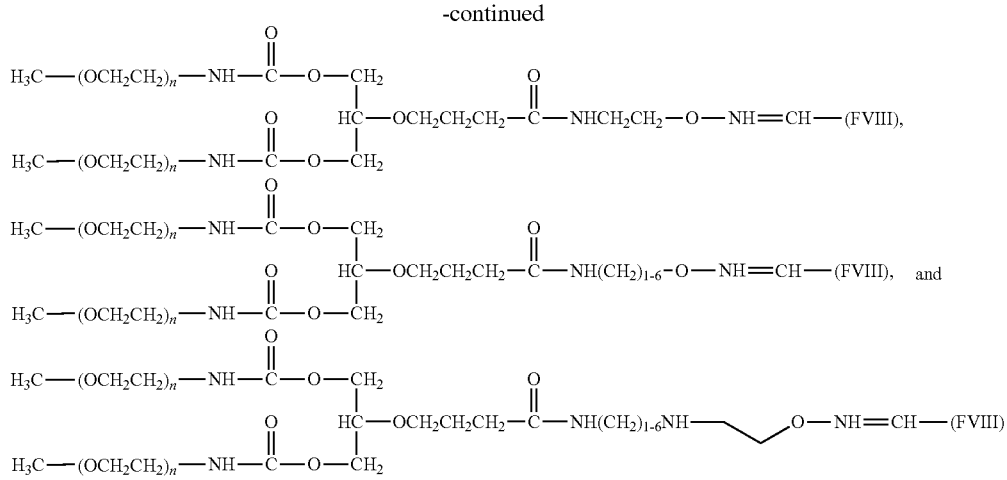

where (m') or (n) for each of the branched structures above typically ranges from about 1 to about 4,000, or from about 1 to about 3,000, or from 1 to about 2,000, preferably from about 20 to about 1,000. In some embodiments, the each of the PEG "arms" have a molecular weight of about 10,000 daltons, such that (m') is about 227 in each of the PEG arms.

Also provided herein is a method of preparing a branched polyethylene glycol oxyamine, as described in detail in Examples 1-3. In the method, a branched reverse urethane PEG reagent, typically activated as an active ester such as an NETS-ester (although any suitable active ester may be used), is reacted with a diamine such as, for example, $H_2N(CH_2)_{1-6}NH_2$, to provide the corresponding reverse urethane PEG carboxamide-amine intermediate. See the general reaction scheme provided below.

inert atmosphere. Typical reaction times include from about 1 hour to about 10 hours, or for about 1 hour to about 8 hours, and the reaction is generally carried out at temperatures ranging from 0° C. to about 60° C. Preferably, the reaction is carried out at room temperature (about 20° C. to about 25° C.). The intermediate RU-PEG2 carboxamide amine intermediate is then recovered, e.g., by precipitation with alcohol (e.g., isopropyl alcohol) and suitably dried. See, for additional details, Example 1, in which the reaction is carried out with ethylene diamine. The RU-PEG2 carboxamide amine intermediate is then reacted with carboxy-protected 2-(carbonylaminooxy)acetic acid using conventional coupling chemistry and conditions (e.g., in the presence of a coupling agent such as N-(3-dimethylaminopropyl)-N'-ethylcarbodiimide hydrochloride in the presence of N,N-dimethylpyridine) to provide the corresponding pro-

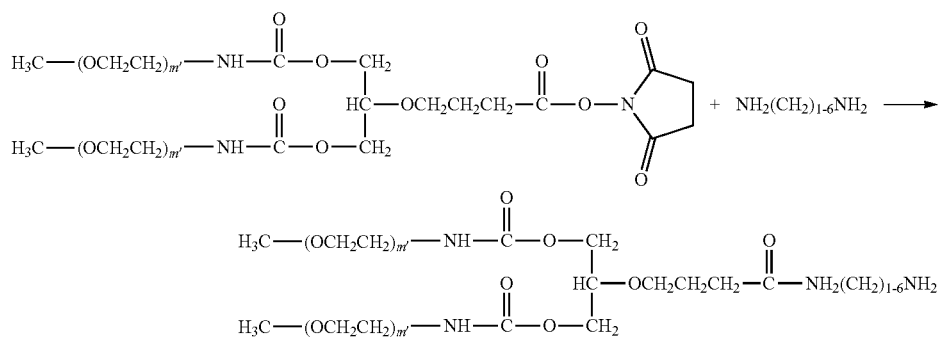

The reaction is typically carried out in an organic solvent, such as, for example, dichloromethane or chloroform, in the presence of base, e.g., triethyl amine. Preferably, the reaction is carried out with dry (i.e., anhydrous) solvent under an tected oxyamine product, where any suitable protecting group may be used. Provided below is an illustrative protected RU-PEG2-oxyamine product comprising the t-Boc protecting group.

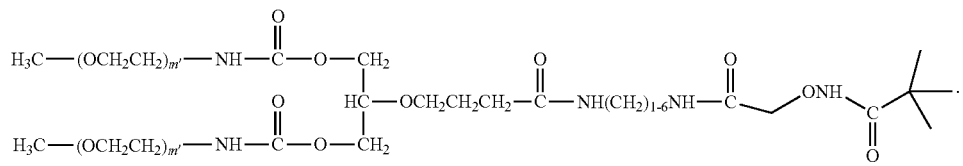

The protecting group is then removed, e.g., with trifluoroacetic acid in the case of the t-Boc protecting group, to provide the desired product. The product is typically recovered by precipitation with alcohol, e.g, isopropyl alcohol, as described above, and has the following structure:

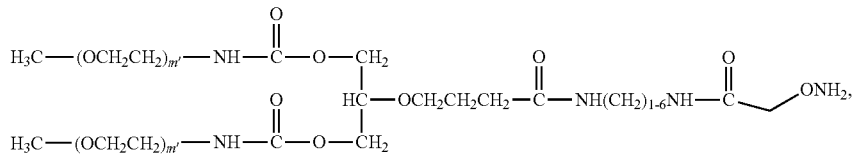

including salt forms thereof.

Also provided herein is a method of preparing a Factor VIII moiety conjugate comprising the step of contacting a polymeric reagent bearing an oxyamine group with a Factor VIII moiety under conditions suitable to form a covalent oxime attachment between the polymer, e.g., PEG moiety, and the biologically active agent, i.e., Factor VIII. Typically, the polymer reactant, that is, the polymer oxyamine, is reacted with the Factor VIII moiety at an equimolar amount (with respect to the desired number of groups suitable for reaction with the reactive group) or at a molar excess. See, for example, the supporting examples. For example, the polymeric reagent can be added to the target active agent at a molar ratio of about 1:1 (polymeric reagent:active agent), 1:1, 1.5:1, 2:1, 3:1, 4:1, 5:1, 6:1, 8:1, 10:1, 20:1, 30:1, 40:1 or even greater. The conjugation reaction is allowed to proceed until a desired degree of polymer attachment has occurred, or until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily, purified to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

For example, and as described in representative Examples 4, 5 and 6, Factor VIII is generally first activated for reaction with a water soluble polymer oxyamine reagent, e.g., a PEG oxyamine, by incubating the Factor VIII moiety with a chemical oxidizing agent such as a periodate (e.g., sodium periodate), to thereby oxidize one or more carbohydrates on Factor VIII. For example, the oxidizing agent is added to a solution of the Factor VIII moiety in a suitable buffer, typically at a pH of about 6. Representative concentrations of the Factor VIII moiety range from about 1.0 mg/mL to about 7 mg/mL, or from about 2.0 mg/mL to about 5 mg/mL, or at about 3-4 mg/mL in a suitable buffer (e.g., comprising HEPES, sodium chloride, calcium chloride, and Tween 80). The oxidation is preferably carried out in the absence of light, e.g., in the dark. The reaction is then allowed to proceed for a suitable period of time, e.g., between about 10 minutes and about 2 hours, preferably for no longer than about 1 hour, or for about 30 to about 45 minutes, sufficient to allow oxidation of carbohydrate groups in the protein but not to result in a significant loss of activity. The oxidation is typically carried out at a temperature ranging from about 5° C. to about 35° C., or from about 5° C. to about 25° C. The oxidized Factor VIII, i.e., having one or more carbohydrates oxidized to provide reactive aldehyde groups suitable for reaction with a PEG oxyamine, is then recovered and confirmed to have maintained its bioactivity using a suitable bioactivity assay, e.g., to measure clotting activity.

Oxidized Factor VIII thus prepared is then reacted with a water-soluble polymer oxyamine such as a PEG oxyamine as described previously herein. For example, oxidized Factor VIII, generally but not necessarily in molar excess relative to the oxidized Factor VIII moiety (e.g., from about equimolar to a 250-molar excess, e.g., at a 5-fold, 10-fold, 30-fold, 50-fold, 70-fold, 100-fold, 120-fold, 150-fold, 200-fold and 300-fold molar excess, explicitly including ranges arrived at by a combination of any two of the foregoing. The oxime-coupling reaction is generally carried out for a time period between about 0.5 hours and about 24 hours, or from about 1 hour to about 8 hours, a temperature between about 2° C. and about 35° C. (e.g., at room temperature from about 20-25° C.

In some embodiments, the coupling reaction between the water soluble polymer oxyamine reagent and the Factor VIII moiety is carried out in the absence of a catalyst selected from o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine. In some particular embodiments, the coupling reaction between the water-soluble polymer oxyamine reagent and the Factor VIII moiety is carried out in the absence of a toluidine. In some other embodiments, the reaction is carried out in the absence of aniline.

Desirably, unreacted aldehyde groups remaining on the oxidized Factor VIII moiety are then capped (i.e., rendered unreactive) by addition of a suitable capping agent such as, for example, an alkoxyamine such as methoxylamine hydrochloride (e.g., in sodium hydroxide such as 1N sodium hydroxide). The resulting reaction mixture is then allowed to react for an additional period of time, e.g., from about 10 minutes to about 5 hours, or from about 15 minutes to 2 hours, or from about 15 minutes to 1 hour. Following the capping reaction, the pH of the reaction mixture may be further adjusted to about pH 7 by addition of a suitable buffer. The resulting PEG-oxime-Factor VIII conjugate mixture may then be further purified by any of a number of suitable methods. Suitable purification methods include, for example, chromatography, filtration and precipitation. Illustrative chromatographic methods include, for example, hydrophobic interaction chromatography (HIC), ion exchange chromatography (IEC), size exclusion chromatography (SEC), affinity chromatography, and reversed-phase chromatography, where a preferred method of purification is anion exchange chromatography.

As described above, if desired, the degree of conjugation (i.e., degree of PEGylation for a PEG oxyamine reagent) can be adjusted by (for example) adjusting reaction conditions. For example, differently numbered polymer (i.e., PEG)-to-FVIII ratios (e.g., 1-mer, 2-mer, 3-mer, and so forth, wherein "1-mer" indicates 1 polymer to Factor VIII moiety, "2-mer" indicates two polymers per Factor VIII moiety, and so on) can be obtained by stopping the conjugation reaction prior to reaching completion, or changing the molar ratios of PEG oxyamine to Factor moiety, and so forth. The conjugation reaction can be stopped in a variety of ways, including, for example, adding a quenching agent (e.g., quenching with an alkoxyamine, such as methoxyamine).

It is possible to characterize the degree of polymer attachment (that is, the number—often expressed in terms of an average number in the context of a composition of conjugates—of polymeric reagents that are attached to carbohydrate moieties of the Factor VIII by virtue of reaction of one or more oxidized carbohydrates (e.g., aldehyde) of the Factor VIII with a PEG oxyamine) of a conjugate. To determine the average number of water-soluble polymer molecules covalently attached to a Factor VIII moiety conjugate, analytical techniques such as SDS-PAGE, SEC, IEC, MALDI-TOF, and so forth can be used. An exemplary approach for determining degree of PEGylation is described in Example 4. In the method employed, the PEG-oxime-Factor VIII conjugate composition is digested, for example, with a protease such as pronase, to desirably exhaustively digest the Factor VIII and thereby release the PEG-moieties that had been covalently attached thereto. The amount of released water-soluble polymer, e.g., PEG, is then quantified using an appropriate method such as SEC-HPLC, or RP-HPLC, or the like.

The methods provided herein are effective to provide Factor VIII-PEG oxime conjugates wherein the PEG (or more generally water soluble polymer) is covalently attached to a carbohydrate of the Factor VIII moiety via an oxime-containing linkage. As can be seen by the supporting examples, illustrative conjugates (and conjugate compositions) having both relatively high and low average degrees of PEGylation have been prepared, e.g., ranging from about 1 to about 20. For the Factor VIII-linear PEG oxime carbohydrate-based conjugates, average degrees of PEGylation for the compositions are in a range of from about 4 to about 20. Preferred compositions of Factor VIII-linear PEG oxime carbohydrate-based conjugates possess an average degree of PEGylation from about 3 to about 8, or more preferably from about 4 to about 7. That is to say, in some embodiments, a preferred composition comprises Factor VIII-linear PEG oxime carbohydrate-based conjugates according to the following structure: $[CH_3O—CH_2CH_2O—(CH_2CH_2O)_{m'}—CH_2CH_2—O—NH=CH]_{3-8}$-(FVIII), where m' is as previously described. In some further embodiments, a preferred composition comprises Factor VIII-linear PEG oxime carbohydrate-based conjugates according to the following structure: $[CH_3O—CH_2CH_2O—(CH_2CH_2O)_{m'}—CH_2CH_2—O—NH=CH]_{4-7}$-(FVIII), where m' is as previously described. In some additional embodiments of the foregoing, the average degree of PEGylation is about 6. An illustrative composition comprises conjugates according to the foregoing structure, where the polyethylene glycol chains covalently attached to carbohydrate moieties on the Factor VIII each have an average molecular weight of about 20,000 daltons.

Turning now to illustrative branched RU-PEG-2 oxime-Factor VIII conjugates and related compositions, average degrees of PEGylation for the compositions are somewhat lower, e.g., in a range of from about 0.5 to about 4, or from about 1 to about 3.5. In some embodiments, the molecular weight of each of the PEG chains in the following structures is about 10,000 daltons.

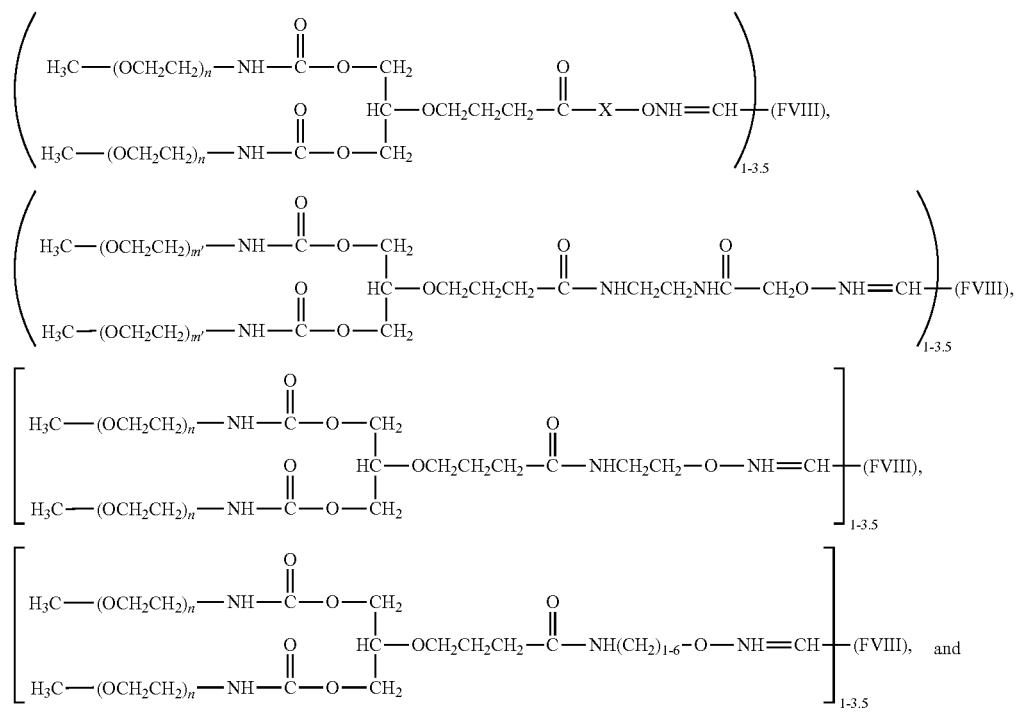

-continued

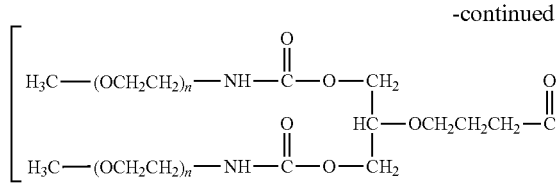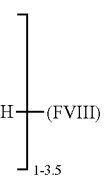

The Factor VIII conjugates and compositions provided herein surprisingly retain a significant degree of biological activity when compared to unmodified Factor VIII moiety based upon any suitable bioassay for measuring Factor VIII biological activity. Preferred PEG-oxime-Factor VIII conjugates retain from about 45% to about 75% or greater, or from 50% to 75% or greater of biological activity, e.g., based upon any suitable bioassay such as, for example, a 1-stage APTT-based clotting assay, when compared to unmodified Factor VIII moiety.

A challenge in providing a therapeutically useful conjugate of Factor VIII is to arrive at a therapeutically useful balance of half-live and bioactivity. Particularly preferred conjugates and related compositions are those having an average number of polymer attachment sites per Factor VIII moiety as described above for linear PEG oximes, e.g., from 3-8, or from 4-7, or about 6, and which retain from about 40% to about 75% or greater biological activity, based upon any suitable assay such as a 1-stage APTT-based clotting assay) when compared to unmodified Factor VIII moiety. Additional preferred conjugates and compositions are those having an average number of branched polymer attachment sites per Factor VIII moiety, e.g., using a branched reverse urethane PEG oxyamine reagent as described previously, e.g., from 0.5 to about 4, or from about 1-3.5, and which retain about 60% or more biological activity, e.g., from about 60% to about 80%, based upon any suitable assay such as a 1-stage APTT-based clotting assay) when compared to the unmodified Factor VIII moiety.

With respect to the Factor VIII-PEG oxime-containing conjugates, the conjugates can be purified to obtain/isolate different conjugated species (through, for example, ion exchange using resins designed for purifying polymer-conjugated drugs, such as MACROCAP brand of ion exchangers available from GE Healthcare Bio-Sciences AB, Uppsala, Sweden). Alternatively, and more preferably for lower molecular weight (e.g., less than about 20 kiloDaltons, more preferably less than about 10 kiloDaltons) polymers, the product mixture can be purified to obtain the distribution of water-soluble polymer segments per Factor VIII. For example, the product mixture can be purified to obtain an average of anywhere from one to five PEGs per active agent (e.g., Factor VIII polypeptide). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography (which approach works best when the polymer size is relatively close to the active agent size). That is to say, gel filtration chromatography is used to fractionate differently numbered polymer-to-active agent ratios (e.g., 1-mer, 2-mer, 3-mer, and so forth) on the basis of their differing molecular weights (where the difference corresponds essentially to the average molecular weight of the water-soluble polymer segments). For example, in an exemplary reaction where a 100 kDa protein is randomly conjugated to a polymeric reagent having a molecular weight of about 20 kDa, the resulting reaction mixture will likely contain unmodified protein (MW 100 kDa), mono-PEGylated protein (MW 120 kDa), di-PEGylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, NJ). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) dye-based methods (e.g., BCA) using BSA as a standard to determine protein content, (iii) iodine testing for PEG content [Sims et al. (1980) Anal. Biochem, 107:60-63], and (iv) sodium dodecyl sulfate polyacrylamide gel electrophoresis (SDS PAGE), followed by staining with barium iodide.

In addition, ion exchange chromatography be used to separate differently numbered polymer-to-active agent ratios (e.g., 1-mer, 2-mer, 3-mer, and so forth). To separate differently numbered polymer-to-protein ratios using ion exchange chromatography the conjugate-containing composition can be eluted through the column with non-conjugated (i.e., unreacted) polymer eluting first, followed by higher, multiply conjugated species, followed by progressively lower multiply conjugated species, and then finishing with non-conjugated proteins.

Separation of positional isomers is carried out by reverse phase chromatography using a reverse phase-high performance liquid chromatography (RP-HPLC) $C_{18}$ column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers). In addition to other techniques, peptide mapping can be used to help determine the location of polymer attachment on the active agent.

Factor VIII-water-soluble polymer conjugates comprising an oxime linkage to carbohydrates on the Factor VIII moiety exhibit increased in vivo half-lives as compared to their corresponding non-conjugated versions. The increase in the in vivo half-life can be assessed by measuring the pharmacokinetics of the conjugate and Factor VIII moiety prior to conjugation in Factor VIII deficient mice as described in the literature. Briefly, Factor VIII deficient mice can be treated with a bolus injection of Factor VIII or Factor VIII-water-soluble polymer conjugate, and Factor VIII antigen levels are measured in plasma samples at various time points. Factor VIII antigen can be measured via ELISA assay. Preferred conjugates and compositions will possess a significant measure of Factor VIII activity, e.g., retention of at least about 30% or more preferably at least about 40% of the unmodified Factor VIII moiety, along with a circulating half-life that is extended by at least about 1.2 to about 1.5 times over that of unmodified Factor VIII.

In some embodiments, and when employing full-length Factor VIII, or a non-B-domain deleted Factor VIII, the corresponding PEG-oxime-Factor VIII conjugates will possess a considerable number of PEG oxime attachment sites in the B-domain, based upon the number of glycosylation sites present in the B-domain of Factor VIII. See, e.g., Lenting, P. J., et al., *Haemophilia* (2010), 16, 6-15. For example, in some embodiments, all of the PEG oxime attachments in the conjugate composition are located in the B-domain of Factor VIII. In yet other embodiments, on average, 90% or more of the PEG oxime attachments are in the B-domain. In yet some other embodiments, on average 80% or more of the PEG oxime attachments are in the B-domain.

The present disclosure also includes pharmaceutical preparations comprising a conjugate or composition as provided herein in combination with one or more pharmaceutically acceptable excipients. Generally, the conjugate itself will be in a solid form (e.g., a precipitate, lyophilate, and so forth), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimerosal, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, NJ); sorbitan esters; lipids, such as phospholipids such as lecithin and other phosphatidylcholines, phosphatidylethanolamines (although preferably not in liposomal form), fatty acids and fatty esters; and steroids, such as cholesterol.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the water-soluble polymer oxime-Factor VIII conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, NJ (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a water-soluble polymer oxime-Factor VIII conjugate as provided herein to a patient suffering from a condition that is responsive to treatment with conjugate such as hemophilia A. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. For example, an exemplary dosing regimen includes administering a PEG-oxime Factor VIII conjugate as provided herein at a dose ranging from about 10 to 90 IU/kg, or from about 15 to 80 IU/kg, or from about 20 to 75 IU/kg, where for each dosage amount, the conjugate is administered, for example, once every month, once every two weeks, once very week, or even twice weekly.

The method of administering may be used to treat any condition that can be remedied or prevented by administration of the conjugate. Those of ordinary skill in the art appreciate which conditions a specific conjugate can effectively treat. For example, the conjugates can be used to treat individuals suffering from hemophilia A. In addition, the conjugates are suited for use as a prophylactic against uncontrolled bleeding, in a patient suffering or not suffering from hemophilia. Thus, for example, the conjugate can be administered to a patient at risk for uncontrolled bleeding prior to surgery.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are hereby incorporated by reference in their entireties.

EXAMPLES

The practice of the invention will employ, unless otherwise indicated, conventional techniques of protein chemistry and the like, which are understood by one of ordinary skill in the art and are explained in the literature. In the following examples, efforts have been made to ensure accuracy with respect to numbers used (e.g., amounts, temperatures, and so forth), but some experimental error and deviation should be accounted for. Unless otherwise indicated, temperature is in degrees Celsius and pressure is at or near atmospheric pressure at sea level. All reagents were obtained commercially unless otherwise indicated.

The Factor VIII used in the following illustrative PEGylation reactions was commercially available full length Factor VIII (ADVATE, Shire) at 3.57 mg/ml in 20 mM HEPES, 0.75 M NaCl, 2 mM $CaCl_2$), 0.1% Tween 80, pH 7.1. Hereinafter, this composition is referred to as the "FVIII solution."

Protein concentrations were determined using the BCA protein assay (Pierce) with BSA as the standard.

The following abbreviations will be used.

Example 1

Preparation of Reverse Urethane(RU)-PEG2-Amine, 20 kD

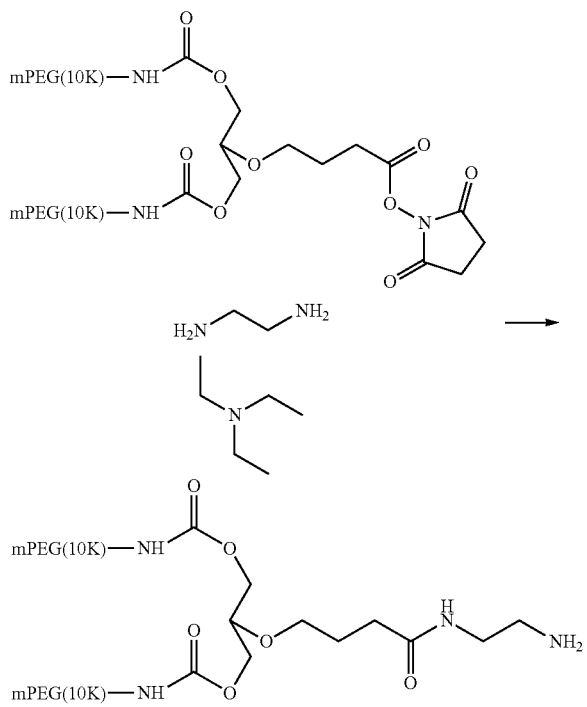

To a solution of ethylenediamine (1.20 g, 0.0200 moles) and triethylamine (1.01 g, 0.0200 moles) in anhydrous dichloromethane (200 ml), solid reverse urethane PEG2-NHS 20K (far left in reaction scheme, 20.0 g, 0.0020 moles) was added during 30 min and the mixture was stirred overnight at room temperature under nitrogen atmosphere. Next the mixture was filtered, concentrated under reduced pressure and added to 600 mL of isopropyl alcohol. The precipitated product was filtered off and dried under vacuum. Yield 19.2 g.

NMR analysis confirmed the structure of the reverse-urethane PEG2-amine-20 kD product.

Example 2

Preparation of t-Boc Protected Reverse Urethane PEG2-Oxymine, 20 kD

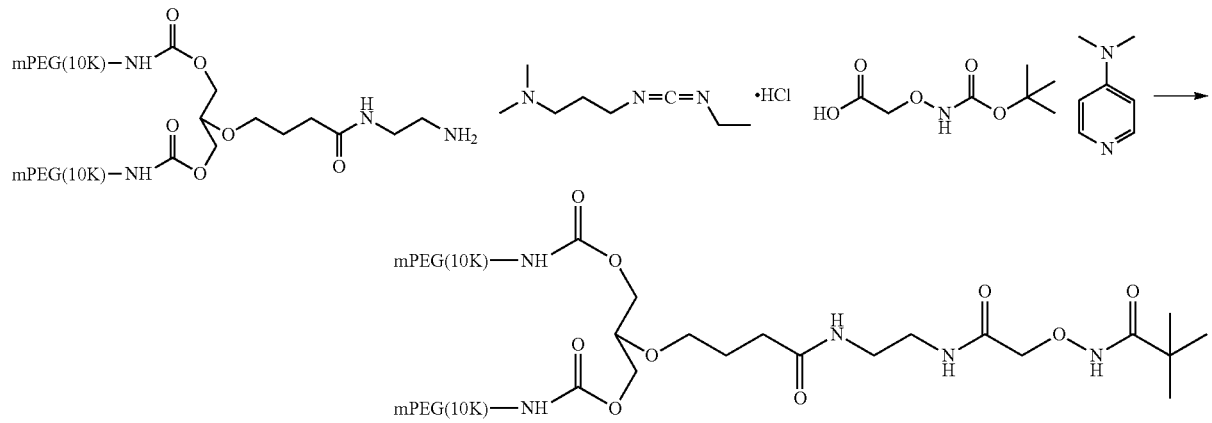

To a solution of RU-PEG2-Amine 20K (19.2 g, 0.0019 moles) in anhydrous dichloromethane (500 ml), 2-(tert-butoxycarbonylaminooxy)acetic acid (0.367 g, 0.0019 moles) was added following by addition of N-(3-dimethylaminopropyl)-N'-ethylcarbodiimide hydrochloride (0.368 g, 0.0019 moles) and N,N-dimethylpyridine (0.059 g, 0.0048 moles). The mixture was stirred overnight at room temperature under nitrogen atmosphere next it was filtered, concentrated under reduced pressure and added to 500 mL of isopropyl alcohol. The precipitated product was filtered off and dried under vacuum. Yield 19.2 g.

NMR analysis confirmed the structure of the obtained compound.

Example 3

Preparation of Reverse Urethane PEG2-Oxyamine, 20 kD

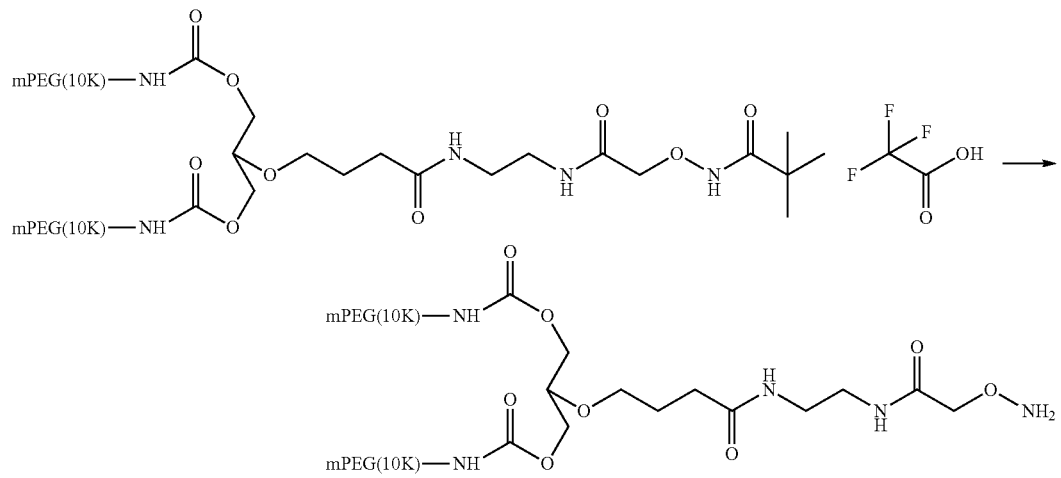

A solution of t-Boc protected reverse urethane PEG2-Oxymine 20K (19.2 g, 0.0019 moles) in a mixture of anhydrous dichloromethane (100 mL) and trifluroacetic acid (100 mL) was stirred overnight at room temperature. Next the solution was concentrated under reduced pressure and added to 500 mL of isopropyl alcohol. The precipitated product was filtered off and dried under vacuum overnight. Yield 19.2 g. (white powder, Mn=21946, polydispersity 1.004).

NMR analysis confirmed the structure of the obtained compound.

Example 4

Carbohydrate PEGylation of Full-Length rFVIII with Linear mPEG$_{20kD}$-Oxyamine The Factor VIII used in the exemplary PEGylation reaction was commercially available full length Factor VIII (ADVATE, Shire) at 3.57 mg/ml in 20 mM HEPES, 0.75 M NaCl, 2 mM CaCl$_2$), 0.1% Tween 80, pH 7.1. Hereinafter, this composition is referred to as the "FVIII solution." Factor VIII was oxidized prior to reaction with an illustrative reactive aminooxy-PEG to convert vicinal diols on the carbohydrates to aldehydes suitable for reaction with the oxyamine PEG reagent.

Oxidation of Factor VIII: Prior to periodate oxidation, the pH of the FVIII solution was adjusted from pH 7.1 to 6.0 with 500 mM IVIES, pH 5.5 solution. A 0.1M, 0.0245 mL solution of freshly prepared sodium periodate solution was transferred into 3.27 ml (3.27 mg/mL) of the pH 6.0 FVIII solution. The reaction mixture was stirred at room temperature in the dark for thirty minutes. After periodate oxidation, the oxidized FVIII samples were buffer exchanged into 20 mM IVIES, 0.15 M NaCl, 2 mM $CaCl_2$), pH 6.0 buffer with a 10 mL Zeba™ spin desalting column according to the manufacturer's instructions. Briefly, columns were centrifuged to remove storage liquid, then three cycles of addition of 5 mL 20 mM MES, 0.15 M NaCl, 2 mM $CaCl_2$), pH 6.0 buffer and centrifugation were performed to equilibrate the column. The oxidized FVIII samples were applied to the spin-column, which was centrifuged again to recover oxidized FVIII in 20 mM IVIES, 0.15 M NaCl, 2 mM $CaCl_2$), pH 6.0 buffer. After buffer exchange, FVIII concentration was determined to be 3.17 mg/mL.

PEGylation and subsequent capping of unreacted aldehyde groups of oxidized FVIII with methoxyamine: A 0.23 mL 100 mg/mL mPEG-20K oxyamine ($CH_3O$—$CH_2CH_2O$—$(CH_2CH_2O)_m$—$CH_2CH_2$—O—$NH_2$, MW 20 kD) solution was added into 3.27 mL, 3.17 mg/ml oxidized FVIII solution (pH 6.0). The reaction mixture was stirred at room temperature for two hours. To cap any unreacted aldehyde groups on the oxidized Factor VIII, 0.23 mL, 100 mg/ml methoxylamine hydrochloride (in 1N NaOH) was added to the PEGylation reaction mixture with additional incubation at room temperature for 15 minutes. Finally, the pH of the reaction mixture was adjusted to 7.1 with 1M Tris, pH 9.0 and diluted with 20 mM Tris, 2 mM $CaCl_2$), until the conductivity was lower than 4.2 ms/cm.

Purifications: An anion exchange chromatography column (HiTrap Q HP, GE Healthcare, 5 mL, Catalog number: 17-1154-01) was used with an AKTA system to purify the PEGylated FVIII conjugate. The elution buffer was 20 mM Tris, 2 mM $CaCl_2$), pH 7.1 (buffer A), and 20 mM Tris, 2 mM $CaCl_2$), 1 M NaCl, pH 7.1 (buffer B). After sample loading, the column was washed with 5 CV buffer A followed by a gradient elution of 0 to 100% B in 10 CV. PEGylated FVIII was pooled and 1 mL of purified PEGylated FVIII saved for degree of PEGylation analysis. Finally, Tween 80 was added to the remainder of purified PEGylated FVIII to a final concentration of 0.1%.

The general approach described above was also employed to prepare Factor VIII conjugates using PEG-5K-oxyamine. Conjugates having different degrees of PEGylation were prepared by varying the molar ratio of PEG-oxyamine to Factor VIII. Generally, higher PEG-to Factor VIII molar ratios resulted in PEG-oxime-Factor VIII conjugates having higher degrees of PEGylation.

Degree of PEGylation (DP) analysis: The definition of degree of PEGylation is the average number of PEG-20K or PEG-5K molecules per FVIII molecule in the conjugate. That is to say, the degree of PEGylation describes the number of PEG molecules covalently attached to the Factor VIII moiety via an oxime-containing linkage (i.e., an oxime linkage) following the PEGylation reaction with the PEG oxyamine and purification. The FVIII-PEG-20K or FVIII-PEG-5K conjugate was digested with a protease (pronase) exhaustively to digest the protein thereby releasing the PEG (and potentially a peptidic residue). The released PEG was quantified with HPLC using the PEG reagents as standards. Briefly, 5 μL, 3 mg/ml pronase (Calbiochem, Catalog number: 53072) was added into 145 μL, 0.61 mg/ml (protein equivalent) of PEGylated FVIII in 20 mM Tris, 2 mM $CaCl_2$), pH 7.1. After incubation at 37 degrees for 24 hours, PEG released from conjugates is quantified with SEC-HPLC coupled with refractive index detector for 20K PEG FVIII conjugates or RP-HPLC coupled with MS detector for 5K PEG FVIII conjugates using the PEG reagents as standards. Using this approach, it was possible to determine the degree of PEGylation.

Multiple lots of Factor VIII-oxime-PEG-20 kD and Factor VIII-oxime-PEG-5dD were prepared and analyzed; conjugates having higher degrees of PEGylation were generally prepared by increasing the molar ratio of PEG oxyamine reagent to Factor VIII. PEG-oxime-20 kD-Factor VIII conjugates were prepared and determined to have degrees of PEGylation in a range between about 4 and 20.

Clotting activities were determined for the conjugates (1-stage APTT based clotting assay; U/mg); the PEG-oxime-20 kD-Factor VIII conjugates retained from about 50 percent to about 75% clotting activity relative to unmodified Factor VIII.

Example 5

Carbohydrate PEGylation of Full-Length rFVIII with Linear $MPEG_{5kD}$-Oxyamine

Linear PEG-5 kD Oxyamine was reacted with carbohydrates on Factor VIII as described in Example 4 above (i.e., oxidation of Factor VIII, PEGylation and capping of unreacted aldehyde functionalities) to prepare the corresponding PEG-5 kD-oxime-Factor VIII conjugates. Certain reactant amounts were varied during the PEGylation reaction (e.g., the ratio of PEG reagent to Factor VIII) to prepare conjugates having different degrees of PEGylation.

Reactant Amounts and Conditions for PEGylation Reactions

| Reaction | 5-A | 5-B | 5-C |
|---|---|---|---|
| Oxidized FVIII (3.1 mg/mL), mL | 3.5 | 3.5 | 3.5 |
| PEG-5K, 100 mg/Ml, mL | 0.058 | 0.135 | 0.29 |
| Molar Ratio (PEG/FVIII) | 30 | 70 | 150 |
| Room temperature, 2 hr, slow stirring | | | |
| $CH_3ONH_2$, 100 mg/mL, mL | 0.058 | 0.135 | 0.29 |
| Room temperature, 15 minutes, slow stirring | | | |

Following the PEGylation reaction, the pH of the reaction mixture was adjusted to 7.1 with 1M Tris, pH 9.0, and the reaction mixture was further diluted with FPLC buffer A to conductivity <4.0 mS/cm (40-60 mL). FPLC purification was carried out using the following eluent system: Column QHP pre-packed, 5 ML. Buffer A: 20 mM Tris, 2 mM CaCl2, pH 7.1/HCl. Buffer B: 20 mM Tris, 2 mM CaCl2, 1 M NaCl, pH 7.1/HCl. Fractions were collected and analyzed to determine degree of PEGylation.

Degree of PEGylation

| Sample | 5-A | 5-B | 5-C |
|---|---|---|---|
| Conc of test article | 0.51 | 0.48 | 0.46 |
| Stock, undiluted (mg/mL) | 1.53 | 1.44 | 1.38 |

| Sample | 5-A | 5-B | 5-C |
|---|---|---|---|
| PEG content* (mg/mL) | 0.16 × 2 = 0.32 | 0.23 × 2 = 0.46 | 0.30 × 2 = 0.6 |
| DP | 12 | 18 | 24 |

Example 6

Carbohydrate PEGylation of Full-Length rFVIII with 20 kD-RU-PEG-oxyamine

Oxidation of Factor VIII: Prior to periodate oxidation, the pH of the FVIII solution was adjusted from pH 7.1 to 6.0 with 500 mM IVIES, pH 5.5 solution. A 0.1M, 0.0592 mL solution of freshly prepared sodium periodate solution was transferred into 7.9 ml (3.27 mg/mL) of the pH 6.0 FVIII solution. The reaction mixture was stirred at room temperature in the dark for thirty minutes. After periodate oxidation, the oxidized FVIII samples were buffer exchanged into 20 mM MES, 0.15 M NaCl, 2 mM $CaCl_2$), pH 6.0 buffer with a 10 mL Zeba™ spin desalting column according to the manufacturer's instructions. Briefly, columns were centrifuged to remove storage liquid, then three cycles of addition of 5 mL 20 mM MES, 0.15 M NaCl, 2 mM $CaCl_2$), pH 6.0 buffer and centrifugation were performed to equilibrate the column. The oxidized FVIII samples were applied to the spin-column, which was centrifuged again to recover oxidized FVIII in 20 mM MES, 0.15 M NaCl, 2 mM $CaCl_2$), pH 6.0 buffer. After buffer exchange, FVIII concentration was determined to be 3.17 mg/mL.

PEGylation and subsequent capping of unreacted aldehyde groups of oxidized FVIII with methoxyamine: A solution of reverse urethane PEG2-Oxymine 20K was added into a solution of oxidized FVIII (pH 6.0). The reaction mixture was stirred at room temperature for about two hours. To cap any unreacted aldehyde groups on the oxidized Factor VIII, methoxylamine hydrochloride (in 1N NaOH) was added to the PEGylation reaction mixture with additional incubation at room temperature for 15 minutes. Finally, the pH of the reaction mixture was adjusted to 7.1 with 1M Tris, pH 9.0 and diluted with 20 mM Tris, 2 mM $CaCl_2$), until the conductivity was lower than 4.2 ms/cm. Reagent amounts and reaction conditions are summarized in the following table for RU-PEG2-oxime-20 kD PEGylation reactions A-D.

Reactant Amounts and Conditions for PEGylation Reactions

| Reaction | 6-A | 6-B | 6-C | 6-D |
|---|---|---|---|---|
| FVIII oxidized, mL | 1.8 | 1.8 | 1.8 | 1.8 |
| PEG-20K-OA, 100 mg/ml, mL | 0.069 | 0.138 | 0.322 | 0.69 |

| Reaction | 6-A | 6-B | 6-C | 6-D |
|---|---|---|---|---|
| Molar ratio PEG/FVIII | 15 | 30 | 70 | 150 |
| Aniline, 100 mM, final ~10 mM | 0 | 0 | 0 | 0 |
| Incubation at room temperature, slow stirring for 100 minutes in dark | | | | |
| $CH_3ONH_2$, 100 mg/ml in 1N NaOH, mL | 0.069 | 0.138 | 0.322 | 0.69 |
| RT, 30 minutes to cap the aldehyde group by $CH_3ONH_2$ | | | | |
| Protein conc. mg/ml(BCA/BSA) | 1.2 mg/ml | 0.98 mg/mL | 1.03 mg/ML | 0.90 mg/mL |
| Protein conc. mg/ml estimated from FPLC | 1.2 mg/ml | 0.90 mg/ml | 0.97 | 0.81 mg/ml |
| HPLC-UV-RI to determine the PEG concentration | | | | |
| DP | 0.5 | 0.7 | 2.0 | 3.5 |

Purifications: An anion exchange chromatography column (HiTrap Q HP, GE Healthcare, 5 mL, Catalog number: 17-1154-01) was used with an AKTA system to purify the PEGylated FVIII conjugate. The elution buffer was 20 mM Tris, 2 mM $CaCl_2$), pH 7.1 (buffer A), and 20 mM Tris, 2 mM $CaCl_2$), 1 M NaCl, pH 7.1 (buffer B). After sample loading, the column was washed with 5 CV buffer A followed by a gradient elution of 0 to 100% B in 10 CV. PEGylated FVIII was pooled and 1 mL of purified PEGylated FVIII saved for degree of PEGylation analysis. Finally, Tween 80 was added to the remainder of purified PEGylated FVIII to a final concentration of 0.1%.

Clotting activities were determined for the conjugates (1-stage APTT based clotting assay; U/mg); the RU-PEG2-oxime-20 kD Factor VIII conjugates retained greater than about 70% clotting activity relative to unmodified Factor VIII.

It is claimed:

1. A polymeric oxyamine reagent having a structure selected from:

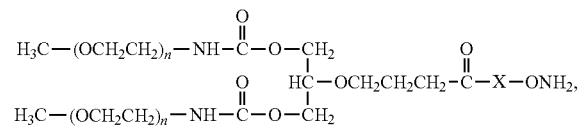

where X is $-NH(CH_2)_{1-6}NHC(O)CH_2-$, and each (n) ranges from about 1 to about 4,000.

2. The polymeric oxyamine reagent of claim 1, wherein X is $-NH(CH_2)_2NHC(O)CH_2-$.

3. The polymeric oxamine reagent of claim 1, wherein each (n) is about 227.

4. The polymeric oxamine reagent of claim 1, wherein each (n) is selected such that the weight average molecular weight of the branched poly(ethylene glycol) polymer ranges from greater than 5,000 Daltons to 100,000 Daltons.

* * * * *